(12) United States Patent
Tsurushita et al.

(10) Patent No.: US 8,969,539 B2
(45) Date of Patent: Mar. 3, 2015

(54) EXPRESSION VECTORS

(75) Inventors: Naoya Tsurushita, Palo Alto, CA (US); J. Yun Tso, Menlo Park, CA (US)

(73) Assignee: JN Biosciences LLC, Palo Alto, CA (US)

(*) Notice: Subject to any disclaimer, the term of this patent is extended or adjusted under 35 U.S.C. 154(b) by 805 days.

(21) Appl. No.: 12/456,007

(22) Filed: Jun. 10, 2009

(65) Prior Publication Data
US 2009/0320149 A1    Dec. 24, 2009

Related U.S. Application Data

(60) Provisional application No. 61/131,657, filed on Jun. 11, 2008.

(51) Int. Cl.
| | |
|---|---|
| *C07H 21/04* | (2006.01) |
| *C12N 15/13* | (2006.01) |
| *C12N 15/63* | (2006.01) |
| *C12N 15/85* | (2006.01) |
| *C12N 5/10* | (2006.01) |
| *C07K 16/00* | (2006.01) |
| *C07K 16/24* | (2006.01) |
| *C07K 16/28* | (2006.01) |

(52) U.S. Cl.
CPC ........... *C07K 16/00* (2013.01); *A01K 2217/072* (2013.01); *A01K 2227/105* (2013.01); *A01K 2267/01* (2013.01); *C07K 16/241* (2013.01); *C07K 16/2866* (2013.01); *C07K 2319/03* (2013.01); *C07K 2319/035* (2013.01); *C07K 2319/30* (2013.01); *C07K 2319/32* (2013.01); *C12N 15/85* (2013.01); *C12N 2840/44* (2013.01); *C12N 2840/85* (2013.01)
USPC .............. 536/23.53; 536/24.1; 435/320.1; 435/325; 435/326; 435/328

(58) Field of Classification Search
CPC ........... C12N 2840/44; C12N 2840/85; C12N 15/85; C12N 2510/00; C07K 2319/30; C07K 16/00
USPC ........... 536/23.53, 24.1; 435/320.1, 325, 326, 435/328
See application file for complete search history.

(56) References Cited

U.S. PATENT DOCUMENTS

| | | |
|---|---|---|
| 2002/0137022 A1 | 9/2002 | Li |
| 2006/0015958 A1* | 1/2006 | Kuroiwa et al. ............... 800/18 |
| 2009/0136950 A1 | 5/2009 | DuBridge et al. |

OTHER PUBLICATIONS

Peterson et al. (1986) PNAS, vol. 83 8883-8887.*
Peterson (2007) Immunol. Res., vol. 37(1), 33-46.*
Peterson et al. (1989) Mol. Cell. Biol., vol. 9, 726-738.*
Peterson et al. (1994) Mol. Cell. Biol., vol. 14, 7891-7898.*
Akamatsu, Y. et al., J. Immunol Methods 327, 40-52 (2007).
Bebbington, C.R. et al., Bio/Technology 10, 169-175 (1992).
Borgnesi, L. and Milcarek, C., Immunol. Res. 36, 27-32 (2006).
Durocher Y., et al., Nucleic Acids Res 30, E9 (2002).
Ho, M. et al., Proc Natl Acad Sci USA 103, 9637-9642 (2006).
Knight, D.M. et al., Mol Immunol 30, 1443-1453 (1993).
Margolskee et al., Mol Cell Biol 8: 2837-2847 (1988).
Martin, A. et al., Proc Natl Acad Sci 99: 12304-12308 (2002).
Mulligan, R.C. and Berg, P., Proc Natl Acad Sci USA 78, 2072-2076 (1981).
Nishinaka, S. et al., J Vet Med Sci 58, 1053-1056 (1996).
Oettinger, M. et al., Science 248: 1511-1523 (1990).
Peterson, M.L., Immunol Res 37, 33-46 (2007).
Peterson, M.L., Mol Cell Biol 14: 7891-7898 (2004).
Rajewsky, K., Nature 381, 751-758 (1996).
Seipelt, R. et al., Mol Cell Biol 18: 1042-1048 (1998).
Sergeeva, A. et al., Adv Drug Deliv Rev 58, 1622-1654 (2006).
Smith, W.J. and Valcarcel, J., Trends Biochem Sci 25, 381-388 (2000).
Spieker-Polet, H. et al., Proc Natl Acad Sci 92, 11840-11845 (1995).
Stam, S. et al., Gene 344, 1-20 (2005).
Winter, G. et al., Annu Rev Immunol 12, 433-455 (1994).
Yanisch-Perron, C. et al., Gene 3:3, 103-119 (1985).
Kohler, G. and Milstein, C., Nature 256, 495-497 (1975).
Sambrook, J. et al., Molecular Cloning, A Laboratory Manual, Cold Spring Harbor Press (book, not included).
International search Report and The Written Opinion of the International Searching Authority, dated Nov. 6, 2009 in PCT/US2009/03502.

* cited by examiner

*Primary Examiner* — Anne Marie S Wehbe
(74) *Attorney, Agent, or Firm* — Don D. Cha; Hamilton DeSanctis & Cha, LLP

(57) ABSTRACT

This present invention provides an expression vector system that uses alternative RNA processing to express in a single cell a polypeptide in both membrane-bound and soluble forms. By incorporating a mimetic structure of the 3' terminal region of human mu gene and introducing other exogenous genetic elements, an artificial gene can be constructed that is capable of simultaneously expressing membrane-bound and secreted forms of polypeptides in myeloma cells and other cells of the B lymphocyte lineage, as well as in non-B cells. If an immunoglobulin heavy chain is co-expressed with a light chain using this vector, whole antibodies can be produced that are both displayed on the surface of a single cell and secreted into the cell culture supernatant. Membrane-bound antibodies facilitate isolation and expansion of those cells displaying antibodies with desired antigen binding characteristics, while secreted antibodies facilitate identification of antibodies having desired biological function(s).

8 Claims, 21 Drawing Sheets

```
                  CH3                    M1                        CD55
M-form  ...ALHNHYTQKSLSLSPEGEVSADEEGFENLWATAST PNKGSGTT SGTT RLL SGHTCFT LTGLLGTLVTMGLLT CH3           S
S-form  ...ALHNHYTQKSLSLSPGK
```

| Clone name | MCF | Ab secretion (µg/ml) |
|---|---|---|
| #1 | 78.53 | 41 |
| #2 | 7.18 | 12 |
| #3 | 22.93 | 7 |
| #6 | 7.09 | 0.5 |
| #9 | 16.70 | 12 |
| #12 | 9.59 | 4.5 |
| #23 | 4.39 | 0 |
| #25 | 11.00 | 10 |
| #26 | 42.79 | 33 |
| #27 | 10.05 | 21 |
| #28 | 10.11 | 6.5 |
| #29 | 3.02 | 0 |
| #30 | 27.63 | 11 |
| #32 | 7.51 | 0.7 |
| #37 | 57.79 | 29 |
| #38 | 12.09 | 3.0 |

Figure 9

| Clone name | MCF | Ab secretion (µg/ml) |
| --- | --- | --- |
| 1B2 | 6.28 | 0.5 |
| 1B3 | 8.78 | 1.6 |
| 1C1 | 8.42 | 1.4 |
| 1D7 | 14.44 | 1.3 |
| 1F8 | 5.21 | 0.3 |
| 1G3 | 3.87 | 0 |
| 1G5 | 13.00 | 2.9 |
| 1G10 | 7.61 | 1.1 |
| 2B8 | 3.90 | 0 |
| 2C6 | 4.94 | 1.5 |
| 2C8 | 4.7 | 0 |
| 3C5 | 4.3 | 0 |
| 3G4 | 36.7 | 5.3 |
| 3G8 | 5.77 | 4.7 |
| 4C4 | 16.3 | 1.9 |
| 4C5 | 10.53 | 2.7 |
| 4D4 | 10.52 | 2.7 |
| 4E5 | 7.83 | 1.9 |
| 4E9 | 3.96 | 0 |
| 4F9 | 5.58 | 2.3 |
| 4G5 | 6.66 | 0.8 |

Figure 12

| Clone name | MCF | Secretion of CD122-Fc (µg/ml) |
| --- | --- | --- |
| 1A2 | 49.8 | 0.38 |
| 1E6 | 4.4 | 0 |
| 1F2 | 44.3 | 0.40 |
| 2C7 | 5.7 | 0 |
| 3A4 | 92.3 | 0.55 |
| 3A6 | 46.4 | 0.44 |
| 3B3 | 132.6 | 0.51 |
| 3B5 | 32.1 | 0.16 |
| 3B9 | 61.7 | 0.31 |
| 3C5 | 29.4 | 0.47 |
| 3C7 | 35.6 | 0.37 |
| 3E2 | 24.8 | 0.32 |
| 3E7 | 27.3 | 0.25 |
| 3E10 | 41.0 | 0.78 |
| 3F4 | 27.6 | 0.56 |
| 3F10 | 40.5 | 0.32 |
| 3H3 | 13.9 | 0.17 |
| 3H4 | 29.3 | 0.33 |
| 3H5 | 47.1 | 0.28 |

Figure 18

SEQUENCE LISTING

```
<160> NUMBER OF SEQ ID NOS: 6

<210> SEQ ID NO 1
<211> LENGTH: 72
<212> TYPE: PRT
<213> ORGANISM: Artificial Sequence
<220> FEATURE:
<223> OTHER INFORMATION: Amino Acid sequence of the C-terminal region of
      the membrane-bound form of gamma heavy chain

<400> SEQUENCE: 1

Ala Leu His Asn His Tyr Thr Gln Lys Ser Leu Ser Leu Ser Pro Glu
1               5                   10                  15

Gly Glu Val Ser Ala Asp Glu Glu Gly Phe Glu Asn Leu Trp Ala Thr
            20                  25                  30

Ala Ser Thr Pro Asn Lys Gly Ser Gly Thr Thr Ser Gly Thr Thr Arg
        35                  40                  45

Leu Leu Ser Gly His Thr Cys Phe Thr Leu Thr Gly Leu Leu Gly Thr
    50                  55                  60

Leu Val Thr Met Gly Leu Leu Thr
65                  70

<210> SEQ ID NO 2
<211> LENGTH: 17
<212> TYPE: PRT
<213> ORGANISM: Artificial Sequence
<220> FEATURE:
<223> OTHER INFORMATION: Amino acid sequence of the C-terminal region of
      the secreted form of gamma-heavy chain

<400> SEQUENCE: 2

Ala Leu His Asn His Tyr Thr Gln Lys Ser Leu Ser Leu Ser Pro Gly
1               5                   10                  15

Lys

<210> SEQ ID NO 3
<211> LENGTH: 19
<212> TYPE: DNA
<213> ORGANISM: Artificial Sequence
<220> FEATURE:
<223> OTHER INFORMATION: Synthethic Oligonucleotide JNT069

<400> SEQUENCE: 3
tccaaagcca aagggcagc                                              19

<210> SEQ ID NO 4
<211> LENGTH: 19
<212> TYPE: DNA
<213> ORGANISM: Artificial Sequence
<220> FEATURE:
<223> OTHER INFORMATION: Synthetic Oligonucleotide JNT061

<400> SEQUENCE: 4
ccgtcgcact catttaccc                                              19

<210> SEQ ID NO 5
<211> LENGTH: 39
```

```
<212> TYPE: DNA
<213> ORGANISM: Artificial Sequence
<220> FEATURE:
<223> OTHER INFORMATION: Synthetic oligonucleotide JNT091

<400> SEQUENCE: 5
agtcagcaag cccatggtta ctagcgtccc aagcaaacc                          39

<210> SEQ ID NO 6
<211> LENGTH: 19
<212> TYPE: DNA
<213> ORGANISM: Artificial Sequence
<220> FEATURE:
<223> OTHER INFORMATION: Synthetic Oligonucleotide JNT037

<400> SEQUENCE: 6
gcagagcctc atgcatcac                                                19
```

EXPRESSION VECTORS

This application claims priority to U.S. Provisional Application 61/131,657, filed Jun. 11, 2008, which is hereby incorporated herein in its entirety.

TECHNICAL FIELD

The invention relates to mutationally altered polynucleotides and polypeptides expressed therefrom, e.g., immunoglobulin heavy chains and Fc fusion proteins, wherein the alteration results in a polypeptide that can be expressed simultaneously in both membrane-bound and secreted forms in eukaryotic cells.

BACKGROUND

Isolation and efficient expression of a specific monoclonal antibody is an essential aspect of modern bioscience, from basic research to development of human therapeutics. There are two methods of isolating a specific monoclonal antibody—the first is hybridoma technology (Kohler, G., and Milstein, C., *Nature* 256, 295-497 (1975) (this and all other references cited herein are hereby incorporated in their entirety herein)) and the second is display technologies using phage, bacteria and yeast (Sergeeva et al., 2006; Winter, G. et al., *Annu Rev Immunol* 12, 433-455 (1994)). Both technologies have their advantages and disadvantages.

Hybridoma technology consists of three main steps: 1) injecting an animal (typically a mouse) with an immunogen to trigger development of B cells producing various antibodies against the immunogen, 2) extracting the animal's B cells and fusing them with an immortal myeloma line (such as Sp2/0-Ag14 or NS0) resulting in a library of immortal, antibody-producing cells called hybridomas, and 3) identifying and isolating those hybridomas from the library that produce monoclonal antibodies with desired binding affinity and/or biological activities, including antibody-dependent cellular cytotoxicity (ADCC), complement-dependent cytotoxicity (CDC), antibody-mediated phagocytosis, apoptosis, cell growth inhibition, cell growth stimulation, and viral neutralization. The advantage of hybridoma technology is that each hybridoma cell line secretes its unique antibody into the growth medium of the cell line, making analyses of the antibody's biological activities relatively easy. The disadvantage of hybridoma technology is that it is not always possible for an immunized mouse to raise high affinity antibodies against certain human antigens or epitopes that are highly conserved between humans and rodents; the mouse's immune system does not recognize such a conserved antigen as "foreign" and does not produce antibodies against it. This is a phenomenon called tolerance (Rajewsky, K., *Nature* 381, 751-758 (1996)). To overcome this problem, non-rodent animals such as rabbits and chickens have been immunized to produce B cells for fusion (Nishinaka, S., et al., *J Vet Med Sci* 58, 1053-1056 (1996); Spieker-Polet, H., at al., *Gene* 344, 1-20 (1995)). However, B cells from rabbits and chickens do not generate immortal hybridomas efficiently, and moreover their resulting hybridomas are generally unstable in antibody production.

An alternative to hybridoma technologies is various display technologies using phage, bacteria cells and yeast cells (Sergeeva, A., et al., *Adv Drug Deliv Rev* 58, 1622-1654 (2006); Winter, G., et al., supra (1994)). In these display technologies, antibody fragments, typically Fab or single-chain Fv (scFv), are expressed on the surface of phage or cells. The phage particles (or cells) are then selected based upon binding affinity to an antigen of interest, and the genes encoding these antibody fragments are recovered from selected phage (or cells). The advantage of display technologies is the ability to create a large antibody fragment library from any species, as long as their variable region sequences are known. The library can be screened to select particular phage particles (or cells) exhibiting antibody fragments with desired antigen binding characteristics on the surface by the use of immobilized antigens. A disadvantage of these display technologies is that the antibody fragments of interest must be converted to the form of intact antibody molecules and expressed in a mammalian expression system to fully characterize their biochemical properties and biological functions, such as binding affinity, ADCC, CDC, antibody-mediated phagocytosis, apoptosis, cell growth inhibition, cell growth stimulation, and viral neutralization. To solve this problem, display technology has recently been used with mammalian cells to enable the isolation (Akamatsu, Y., et al., *J Immunol Methods* 327, 40-52 (2007)) and affinity maturation (Ho, M., et al., *Proc Natl Acad Sci USA* 103, 9637-9642 (2006)) of monoclonal antibodies. In these mammalian cell display systems, human IgG molecules attached to a glycosyl-phosphatidylinositol (GPI) anchor (Akamatsu, Y., et al., supra (2007)) or human scFv fragments fused to the transmembrane domain of a PDGF receptor (Ho, M., et al., supra (2007)) are expressed on the surface of mammalian cells. The advantage of using mammalian cells is that antibody molecules are expressed without folding and post-translational modification problems associated with non-mammalian cells. After selecting cells expressing membrane-bound antibodies with desired antigen binding properties, the genes of these membrane-bound antibodies are recovered from cells and modified to express a secreted form of the antibody. The modified genes are then reintroduced to mammalian cells, and the antibodies secreted into the culture medium of these cells lines can be analyzed for desired biological characteristics.

Thus, currently used display technologies can produce large antibody libraries from a wide range of species from which particular antibodies having desired antigen binding characteristics can be selected, but the genes encoding these selected modified antibodies have to be laboriously manipulated in order to produce intact soluble antibody molecules for analyses of their biological functions. Hybridoma technologies, on the other hand, readily yield soluble antibodies, but are only applicable to a limited number of species. Furthermore, since hybridomas are not physically linked to their secreted antibodies, they cannot be selected by the use of immobilized antigens to which the secreted antibodies may bind. Each hybridoma has to be grown individually, which often requires multiple rounds of subcloning, for detailed analyses of its secreted antibodies.

Therefore, in order to combine the advantages and eliminate the disadvantages of both display and hybridoma technologies, expression of whole antibody molecules by mammalian cells simultaneously in both their membrane-bound and secreted forms is desired. Particularly, it is ideal to express such secreted antibody in its fully intact soluble form. Cells can be selected based on antigen binding of their membrane-bound antibodies. Antibodies secreted in the culture medium of each of the selected cells can be tested for antigen-binding and biological activity without further manipulation of the cell and antibody-encoding genes.

Alternative RNA processing is a common strategy used by eukaryotes to produce more than one mRNA, resulting in more than one kind of polypeptide, from a single transcription unit (Smith, C. W., and Valcarcel, J., *Trends Biochem Sci* 25, 381-388 (2000); Stamm, S., et al., *Gene* 344, 1-20 (2005)). The gene coding for the human immunoglobulin mu heavy chain is one such gene (Peterson, M. L., *Immunol Res* 37, 33-46 (2007)). B lymphocytes produce two distinct forms of IgM molecules during differentiation—the monomeric, membrane-bound form in early-stage B cells and the pentameric, secreted form in terminally differentiated plasma cells. The switch between the synthesis of the two forms of IgM molecules is accomplished by alternative RNA processing of mu heavy-chain precursor RNA. The two forms of mu mRNA differ only in their 3' termini (FIG. 1). Specifically, when the precursor mu RNA is cleaved and polyadenylated using the first poly(A) site located downstream of the CH4 exon (shown as "pA-s" in FIG. 1), the resulting mature mRNA produces the secreted form (S-form) of the mu heavy chain. Alternatively, when the first poly(A) site (pA-s) is removed by splicing between the CH4 and M1 exons, and the second poly(A) site (shown as "pA-m" in FIG. 1) is used, the resulting mRNA produces the membrane-bound form (M-form) of the mu heavy chain. When expressed, the two forms differ in their amino acid sequences at the C-terminal of their respective molecules. Although the molecular mechanism that controls the alternative processing of mu heavy chain mRNA is not fully understood to date (Borghesi and Milcarek, 2006; Peterson, M. L., supra (2007)), delicate balancing between two mutually exclusive RNA processing events, i.e., splicing of precursor mu RNA between the CH4 and M1 exons and its cleavage/polyadenylation at the first poly(A) site (pA-s), seems to be the key for determining the ratio between M-form and S-form of mu mRNA.

By incorporating the gene structure that mimics the 3' region of the mu gene (hereinafter, a "Ig mu gene 3' region mimetic"), which enables generation of two forms of mRNA from a single transcription unit by alternative processing of the common precursor RNA, and adjusting the balance between the two mutually exclusive RNA processing events in such constructed gene, we developed an expression vector capable of simultaneous expressing membrane-bound and secreted forms of a polypeptide in a single eukaryotic cell.

SUMMARY OF THE INVENTION

This invention provides an expression vector system that uses alternative RNA processing to express a polypeptide in both membrane-bound and soluble forms from a single transcription unit in a cell. By incorporating a mimetic structure of the 3' terminal region of the human mu gene and introducing other exogenous genetic elements, an artificial gene can be constructed that is capable of simultaneously expressing membrane-bound and secreted forms of polypeptides, such as immunoglobulin heavy chains and Fc fusion proteins, in myeloma cells and other cells of the B lymphocyte lineage, as well as in non-B cells. If the artificial heavy chain gene is coexpressed with an immunoglobulin light chain, whole antibodies can be produced that are both displayed on the surface of the cell and secreted into the cell culture medium. The membrane-bound polypeptides facilitate detection, enrichment and isolation of particular cells producing polypeptides with desired antigen-, ligand- or receptor-binding properties, while the secreted polypeptides can be characterized for desired biochemical and biological functions (e.g., binding affinity, ADCC, CDC, signal transduction, complex formation, ligand-receptor interaction) without having to perform laborious manipulation of the cells and polypeptide-encoding genes, as is the current practice.

BRIEF DESCRIPTION OF THE DRAWINGS

FIG. 4. The amino acid sequence of the C-terminal coding region of each of the M-form [SEQ ID NO 1] and S-form [SEQ ID NO 2] of the heavy chain produced by the expression vector shown in FIG. 2D.

FIG. 9. Geometrical mean channel fluorescence (MCF) showing expression of M-form IgG molecules and corresponding ELISA analysis showing S-form expression in the growth medium for each NS0 transfectant of FIG. 8.

FIG. 12. Geometrical mean channel fluorescence (MCF) of M-form expression of each NS0 transfectant of the expression vector pQAb109 shown in FIG. 11 along with ELISA analysis of S-form antibody secretion in culture supernatant of each NS0 transfectant.

FIG. 18. Geometrical mean channel fluorescence (MCF) showing expression of M-form Fc fusion proteins and corresponding ELISA analysis showing S-form expression in the growth medium for each NS0 stable transfectant of the expression vector pFCm110 shown in FIG. 17A.

DETAILED DESCRIPTION

Figure 1:
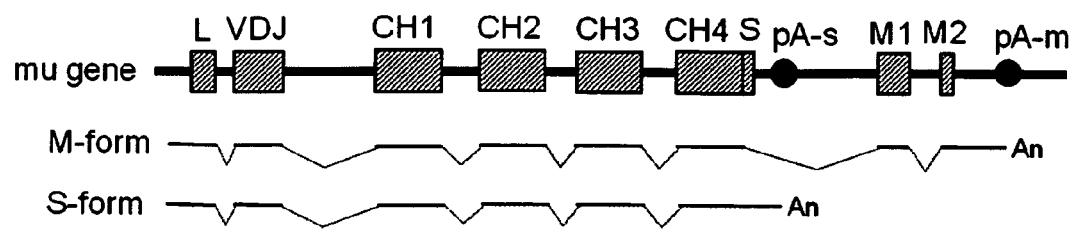
FIG. 1. Schematic drawing of the human immunoglobulin mu heavy chain gene, along with its corresponding precursor RNA processed to membrane-bound form (M-form) and secreted form (S-form) mRNA.

The expression vectors described herein are useful for simultaneous expression of polypeptides in both membrane-bound and secreted forms by alternative RNA processing of the common precursor RNA from a single transcription unit in eukaryotic cells. An advantage of these vectors is that cells simultaneously expressing both membrane-bound and secreted polypeptides can be selected first by the use of immobilized natural or unnatural binding partners, e.g., polypeptides, carbohydrates, lipids, plastics and metals. Polypeptides secreted from each of selected cells in culture medium can then be characterized for their binding properties, biological functions, and molecular characteristics without manipulation of cells and the genes encoding the polypeptides, thus eliminating laborious and time-consuming experimental steps, such as isolation, modification and secondary expression of the genes of interest, associated with the current display technologies.

When membrane-bound and secreted forms of immunoglobulin heavy chains are stably coexpressed with immunoglobulin light chains using these vectors, antibody molecules are expressed simultaneously on cell surface as the membrane-bound form and in culture medium as the secreted form. Thus, these vectors allow selection of cells expressing membrane-bound antibodies with desired binding characteristics by the use of immobilized antigens. Antibodies secreted in culture medium of each of the selected cells are readily used for the analysis of their biological functions, this allowing efficient isolation of monoclonal antibodies with desired binding and biological properties.

EXPERIMENTAL EXAMPLES

Generally, the nomenclature used hereafter and the laboratory procedures in recombinant DNA technology described below are those well known and commonly employed in the art. Standard techniques are used for cloning, DNA and RNA isolation, amplification and purification. Generally, enzymatic reactions involving DNA ligase, DNA polymerase, restriction endonucleases and the like are performed according to the manufacturer's specifications. These techniques and various other techniques are generally performed according to Sambrook, J., et al., Molecular Cloning, A Laboratory Manual, Second edn (Cold Spring Harbor Laboratory Press 1989). The procedures described therein are well known in the art and are provided for the convenience of the reader. All the information contained therein is incorporated herein by reference.

Expression Vectors

The light-chain expression vector pQAb711 (FIG. 2A) was generated to carry the following genetic components using standard molecular biology techniques (Sambrook, J. et al., supra (1989)). Proceeding clockwise from the SalI site at the top, pQAb711 contains the light chain transcription unit starting with the human cytomegalovirus major immediate early promoter and enhancer (CMV promoter; CMV-P) (SalI to NheI) to initiate transcription of the antibody light chain gene. The CMV promoter is followed by an exon encoding a lambda light chain variable region (VL(y3)) (NheI to EcoRI) and a genomic sequence containing the human lambda-2 light chain constant region exon (Cλ) with part of the intron preceding it and a poly(A) site (pA) after Cλ (EcoRI to SphI). The light chain gene is then followed by the transcription unit of E. coli xanthine guanine phosphoribosyl transferase (gpt) (SphI to BamHI) derived from pSV2gpt (Mulligan, R. C., and Berg, P. Proc Natl Acad Sci USA 78, 2072-2076 (1981)) to provide a selectable drug-resistance marker in mammalian cells. The gpt gene is flanked by the SV40 promoter (SV40-P) at the upstream and the SV40-derived poly(A) site (SV40-pA) at the downstream. Finally, pQAb711 contains the replication origin in E. coli (ori) and the beta lactamase gene (amp) derived from pUC19 (Yanisch-Perron, C., et al., Gene 33, 103-119 (1985)) (BamHI to SalI).

Another light-chain expression vector pQAb730 (FIG. 2B) carrying the following genetic components was also constructed. Proceeding clockwise from the ApoI site at the top, pQAb730 has the CMV promoter (ApoI to NheI), the same lambda light chain gene as in pQAb711 (NheI to BamHI) and the transcription unit of the gpt gene derived from pSV2gpt (BamHI to PvuII). The orientation of the gpt gene is different between pQAb711 and pQAb730. Finally, pQAb730 carries the replication origin in E. coli (ori) and the beta lactamase gene (amp) derived from pSV2gpt (PvuII to ApoI).

The heavy-chain expression vector pQAb710 (FIG. 2C) was generated to carry the following genetic components. Proceeding clockwise from the SalI site at the top, pQAb710 contains the CMV promoter to initiate transcription of the antibody heavy chain gene (SalI to SpeI). The CMV promoter is followed by an exon encoding a heavy chain variable region (VH(103.1)) (SpeI to HindIII), a genomic sequence containing the human gamma-1 heavy chain constant region including the CH1, hinge, CH2 and CH3 exons with the intervening introns, and a poly(A) site (pA-s) for mRNA processing following CH3 (HindIII to XbaI). Proceeding clockwise further, pQAb710 contains the replication origin in E. coli (ori) and beta lactamase gene (amp) of pUC18 (Yanisch-Perron, C., et al., supra (1985)) (XbaI to SalI). Only the secreted form of gamma-1 heavy chain (S-form) is produced from the heavy chain gene in pQAb710 (FIG. 3A).

The heavy-chain expression vector pQAb741 (FIG. 2D) was constructed as follows. First, a genomic DNA fragment carrying the M1 and M2 exons of the human mu immunoglobulin gene, the preceding intron sequence, and the downstream poly(A) site (pA-m) was inserted between the SphI and XbaI sites of pQAb710. Next, the Sau3AI-BamHI fragment of pQAb730, which provides the SV40 early poly(A) site (SV40 early pA) in one direction and the SV40 late poly(A) site (SV40 late pA) in another direction, was inserted into the EagI site located downstream the CH3 exon in such a way that the SV40 late poly(A) site is used in the heavy chain transcription unit. Finally, a 3' portion of the M1 exon, the entire M1-M2 intron, and the M2 exon were replaced with the glycosyl-phosphatidylinositol (GPI) membrane anchorage signal derived from the human CD55 gene to generate a hybrid exon (M1-GPI).

Figure 3:
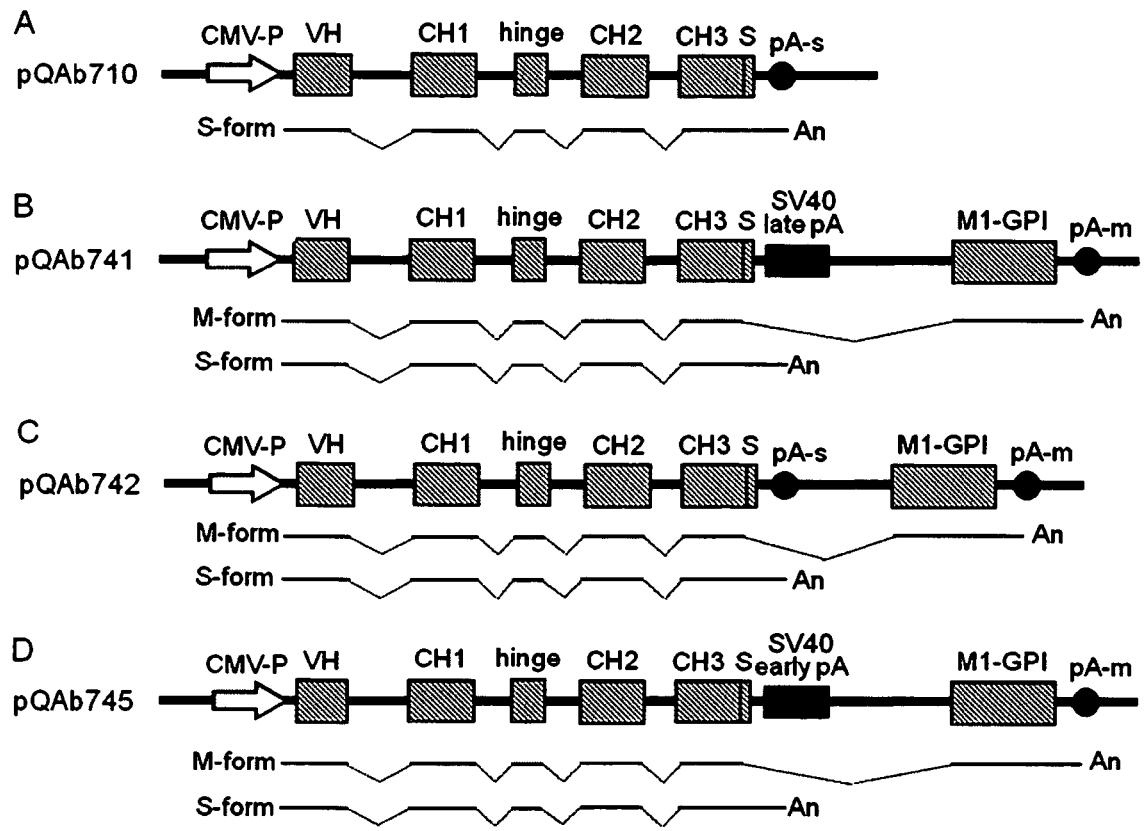
FIG. 3. Schematic representations of the mRNA (M-form and S-form) transcribed from the four immunoglobulin heavy chain expression vectors shown in FIG. 2.

As shown in FIG. 3B, the heavy chain gene in pQAb741 is composed of the genomic sequence encoding the intact soluble form of human gamma-1 heavy chain (VH, CH1, hinge, CH2, CH3 and S) followed by the SV40 late poly(A) site, M1-GPI exon and the second poly(A) site of the human mu gene (pA-m). The region encompassing the CH3 exon, SV40 late poly(A) site, M1-GPI exon, and second poly(A) site (pA-m) mimics the structure of the 3' region of the human mu gene ("Ig mu gene 3' region mimetic"). Two types of mRNA, one for secreted human gamma-1 heavy chain (S-form) and another for membrane-bound heavy chain (M-form), can theoretically be produced by alternative RNA processing from the heavy chain gene in pQAb741. The M-form mRNA is generated when the precursor RNA is spliced between the CH3 and M1-GPI exons and polyadenylated at the poly (A) site located downstream the M1-GPI exon (pA-m). The S-form mRNA is generated when the precursor RNA is cleaved and polyadenylated at the SV40 late poly (A) site located immediately downstream the CH3 exon. These two types of RNA processing, i.e., splicing between the CH3 and M1-GPT exons and cleavage/polyadenylation at the SV40 late poly(A) site, are mutually exclusive. The amino acid sequence of the C-terminal region of each of the membrane-bound and secreted forms of heavy chain produced by pQAb741 is shown in FIGS. 4A and 4B, respectively. Amino acid sequences presented as CH3, M1, CD55, and S in FIGS. 4A and 4B derived from the CH3 region of human immunoglobulin gamma-1 heavy chain, the M1 region of mouse immunoglobulin heavy chain, the C-terminal region of human CD55, and the S region of the human gamma-1 heavy chain, respectively.

The heavy-chain expression vector pQAb742 (FIG. 2E) was constructed by removing the EagI fragment carrying the SV40 late poly(A) site from pQAb741. The heavy-chain expression vector pQAb745 (FIG. 2F) was constructed by reversing the orientation of the EagI fragment in pQAb741 such that the SV40 early poly(A) site is used in the heavy chain transcription unit. Both pQAb742 and pQAb745 can theoretically produce S- and M-forms of heavy chain mRNA by alternative RNA processing (FIGS. 3C and 3D). The amino acid sequence of the membrane-bound form of heavy chain is identical to each other among pQAb741, pQAb742 and pQAb745. The amino acid sequence of the secreted form of heavy chain is identical to each other among pQAb710, pQAb741, pQAb742 and pQAb745.

Expression of IgG in HEK293 Cells

Each of the four heavy-chain expression vectors (pQAb710, pQAb741, pQAb742 and pQAb745) was co-transfected with the light-chain expression vector pQAb730 to human embryonic kidney cell line HEK293 using polyethylenimine according to Durocher et al. (Durocher, Y., et al., *Nucleic Acids Res* 30, E9 (2002)) for production of human IgG/lambda antibodies. Transfected cells were grown in DME medium containing 10% fetal bovine serum (FBS) at 37° C. in a 7.5% $CO_2$ incubator for 2 days. Expression level of IgG/lambda antibodies in culture supernatant was measured by sandwich ELISA using standard procedures. Expression of IgG/lambda molecules on the cell surface was analyzed by flow cytometry following standard procedures.

In a typical sandwich ELISA experiment, a microtiter plate was coated overnight at 4° C. with 100 µl/well of 1/2,000-diluted goat anti-human IgG Fc gamma chain-specific polyclonal antibody (SouthernBiotech, Birmingham, Ala.) in PBS, washed with Wash Buffer (PBS containing 0.05% Tween 20), and blocked for 1 hr at room temperature with 300 µl/well of Blocking Buffer (PBS containing 2% Skim Milk and 0.05% Tween 20). After washing with Wash Buffer, 100 µl/well of samples appropriately diluted in ELISA Buffer (PBS containing 1% Skim Milk and 0.025% Tween 20) were applied to the ELISA plate. Human IgG/lambda antibody purified from human myeloma serum (SouthernBiotech) was used as a standard. After incubating the ELISA plate for 2 hr at room temperature and washing with Wash Buffer, bound antibodies were detected using 100 µl/well of 1/2,000-diluted HRP-conjugated goat anti-human lambda chain polyclonal antibody (SouthernBiotech). After incubating for 1 hr at room temperature and washing with Wash Buffer, color development was performed by adding 100 µl/well of ABTS substrate. Color development was stopped by adding 100 µl/well of 2% oxalic acid. Absorbance was read at 405 nm.

The expression levels of IgG/lambda in culture supernatant of transiently transfected HEK293 cells were 7 µg/ml for cotransfection of pQAb730 and pQAb710, 8 µg/ml for pQAb730 and pQAb741, 9 µg/ml for pQAb730 and pQAb745. No IgG/lambda antibodies were detected in culture supernatant of HEK293 cells transfected with pQAb730 and pQAb742.

In a typical flow cytometry experiment to detect human IgG/lambda molecules on the cell surface, transiently transfected HEK293 cells were treated with 0.05% trypsin for harvesting, washed with FACS Binding Buffer (PBS containing 0.5% BSA and 0.05% $NaN_3$), suspended in 200 µl of FACS Binding Buffer, and mixed with 50 µl of 1/50-diluted FITC-labeled goat anti-human IgG antibody (SouthernBiotech). After 30 min on ice, the cells were washed with FACS Binding Buffer, suspended in 200 µl of FACS Binding Buffer, and analyzed using a FACScan flow cytometer (BD Biosciences, Franklin Lakes, N.J.).

Figure 5:
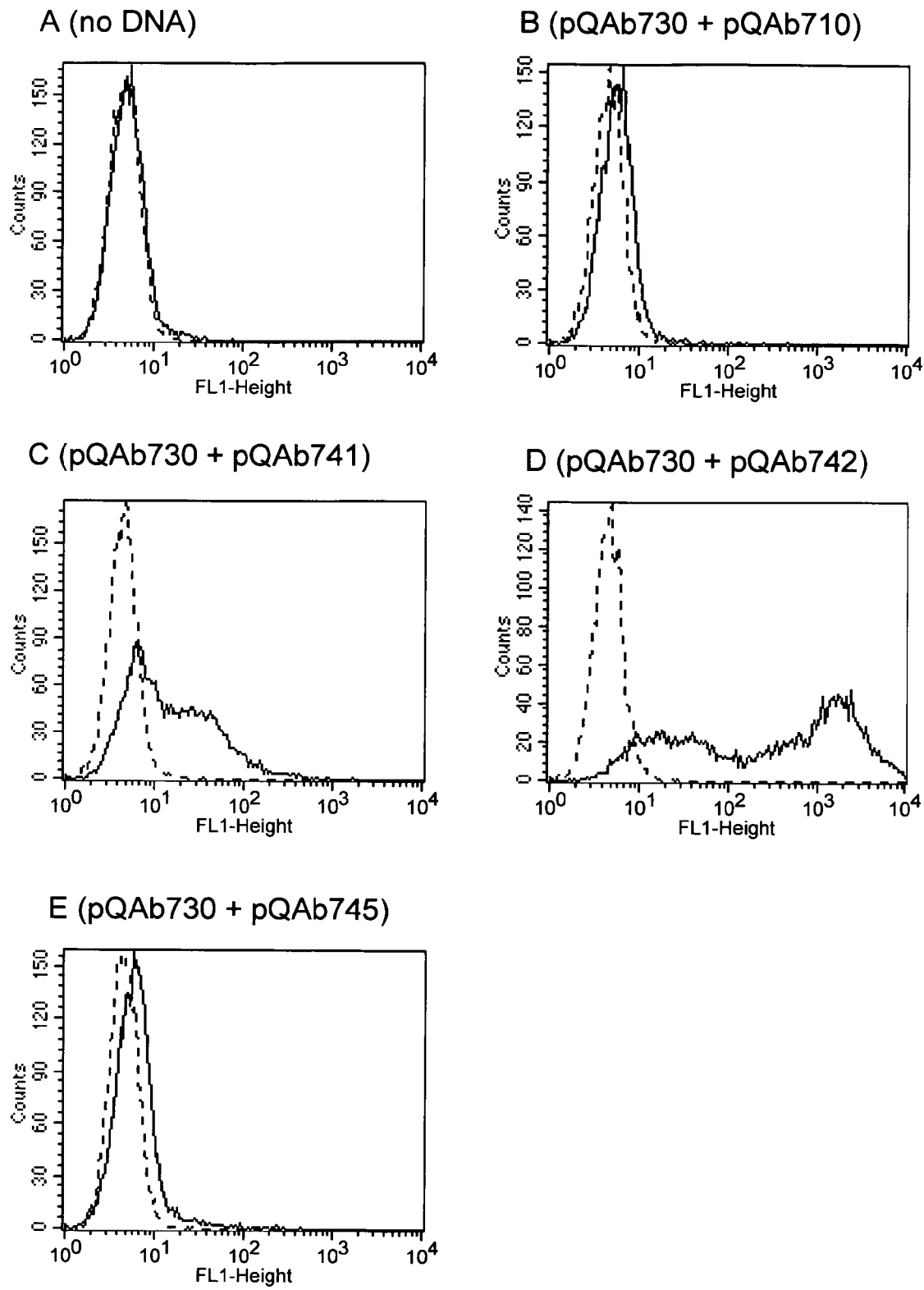
FIG. 5. Flow cytometry analysis of expression levels of control (FIG. 5A) and coexpression of the light chain vector shown in FIG. 2B and the heavy chain vector shown in FIG. 2C (FIG. 5B), the heavy chain vector shown in FIG. 2D (FIG. 5C), the heavy chain vector shown in FIG. 2E (FIG. 5D) and the heavy chain vector shown in FIG. 2F (FIG. 5E).

The result of a representative flow cytometry experiment is shown in FIG. 5. The level of fluorescence of stained cells correlates to the amount of IgG/lambda molecules on the surface. Therefore, if the histogram shifts to the right side compared to the control, the cells are concluded to have IgG/lambda molecules on the surface. When HEK293 cells were cotransfected with pQAb730 and pQAb710, only a slight shift to the right side was observed with the cells stained with FITC-labeled goat anti-human IgG antibody (solid line in FIG. 5B) compared to the cells without staining (broken line in FIG. 5B). Since pQAb710 produces only the secreted form of gamma-1 heavy chain, this level of marginal shift is considered to be a result of non-specific cell staining. A similar level of marginal shift was observed with stained cells when HEK293 cells were transfected with pQAb730 and pQAb745 (FIG. 5E). When HEK293 cells were co-transfected with pQAb730 and pQAb741 (FIG. 5C), a significant level of shift was observed when cells were stained with FITC-labeled goat anti-human IgG antibody (solid line) compared to unstained cells (broken line), indicating that a large number of IgG/lambda molecules are present on the surface. When pQAb730 and pQAb742 (FIG. 5D) were used for co-transfection, a very strong shift was observed with stained cells (solid line) compared to unstained cells (broken line).

A summary of IgG/lambda expression in HEK293 cells with the four kinds of heavy chain expression vectors (pQAb710, pQAb741, pQAb742 and pQAb745) when cotransfected with the light chain expression vector pAb730 is described as follows. With pQAb710 (FIG. 3A) and pQAb745 (FIG. 3D), only the secreted form of IgG/lambda was produced and no membrane-bound form was detected. With pQAb742 (FIG. 3C), no secreted form was detected whereas a high level expression of the membrane-bound form was detected. With pQAb741 (FIG. 3B), both secreted and membrane-bound forms of IgG/lambda were detected. Although the heavy chain gene in each of pQAb741, pQAb742 and pQAb745 can theoretically produce both secreted and membrane-bound forms of heavy chain by alternative RNA processing, only the heavy chain gene in pQAb741 was actually capable of simultaneously producing the secreted and membrane-bound forms in HEK293 cells. The only difference between pQAb741 and pQAb745 is the orientation of the EagI fragment; the SV40 late poly (A) site is used in the heavy chain transcription unit in pQAb741 and the SV40 early poly (A) site is used in pQAb745. The length of the intron between the CH3 and M1-GPI exons is equal between pQAb741 and pQAb745. Thus, subtle difference in the gene structure is important in determining the ratio between the secreted and membrane-bound forms of heavy chain mRNA.

Analysis of Heavy Chain mRNA Expressed in HEK293 Cells

Simultaneous expression of the secreted and membrane-bound forms of heavy chain mRNA in HEK293 cells transfected with pQAb741 was confirmed by RT-PCR. HEK293 cells were transiently cotransfected with pQAb730 and pQAb741, which together produce both secreted and membrane-bound forms of IgG molecules, using the polyethylenimine method (Durocher et al., supra (2002)) as described above. As a control, pQAb730 and pQAb710, which together produce only the secreted form of IgG, were cotransfected to HEK293 cells. Transfected cells were grown in DME medium containing 10% fetal bovine serum (FBS) at 37° C. in a 7.5% CO2 incubator for 2 days. Total RNA was extracted from the cells using TRIzol reagent (Invitrogen, Carlsbad, Calif.) and oligo dT-primed cDNA was synthesized using the SuperScript III First-Strand Synthesis System for RT-PCR (Invitrogen) following the suppliers' protocols.

Figure 6:
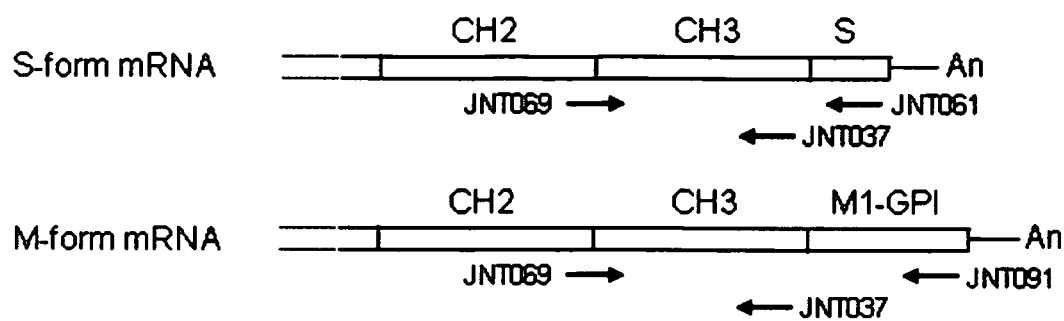
FIG. 6. Schematic representation of the location of RT-PCR primer sequences for amplification of the S-form and M-form immunoglobulin heavy chain mRNA (FIG. 6A), and the result of the RT-PCR analysis (FIG. 6B).
Figure 6:
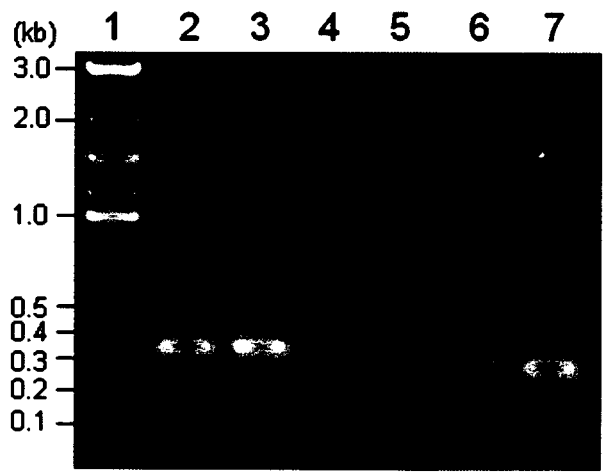

The location and orientation of each of the PCR primers used in the RT-PCR experiment is illustrated in FIG. 6A. In the RT-PCR experiment shown in FIG. 6B, cDNA derived from HEK293 cells cotransfected with pQAb730 and pQAb710, thus producing only the secreted form of IgG antibodies, was used in lanes 2, 4 and 6, and cDNA derived from HEK293 cells cotransfected with pQAb730 and pQAb741, thus producing both secreted and membrane-bound forms of IgG antibodies, was used in lanes 3, 5 and 7. For detection of the secreted form of heavy chain mRNA in the RT-PCR experiment, JNT069 (5'-TCCAAAGC-CAAAGGGCAGC-3') [SEQ ID NO 3], which bind to the junction between the CH2 and CH3 exon, was used as a 5' primer and JNT061 (5'CCGTCGCACTCATTTACCC-3') [SEQ ID NO 4], which bind to the 3' region specific for the secreted form (S region), was used as a 3' primer (lanes 2 and 3). For detection of the membrane-bound form of heavy chain mRNA, JNT069 was used as a 5' primer and JNT091 (5'AGT-CAGCAAGCCCATGGTTACTAGCGTC-CCAAGCAAACC-3') [SEQ ID NO 5], which bind to the M1-GPI exon, was used as a 3' primer (lanes 4 and 5). For detection of both secreted and membrane-bound forms of mRNA at the same time, JNT069 was used as a 5' primer and JNT037 (5'GCAGAGCCTCATGCATCAC-3') [SEQ ID NO 6], which bind to the CH3 exon, was used as a 3' primer (lanes 6 and 7). As size markers, 2-log ladder (New England Biolabs) was used in lane 1. Only the secreted form of heavy chain mRNA was detected when HEK293 cells were transfected with pQAb710 (lanes 2, 4 and 6). When HEK293 cells were transfected with pQAb741, both secreted and membrane-bound form of heavy chain mRNA were produced (lanes 3, 5 and 7).

Expression of IgG in NS0 Cells

Figure 2:
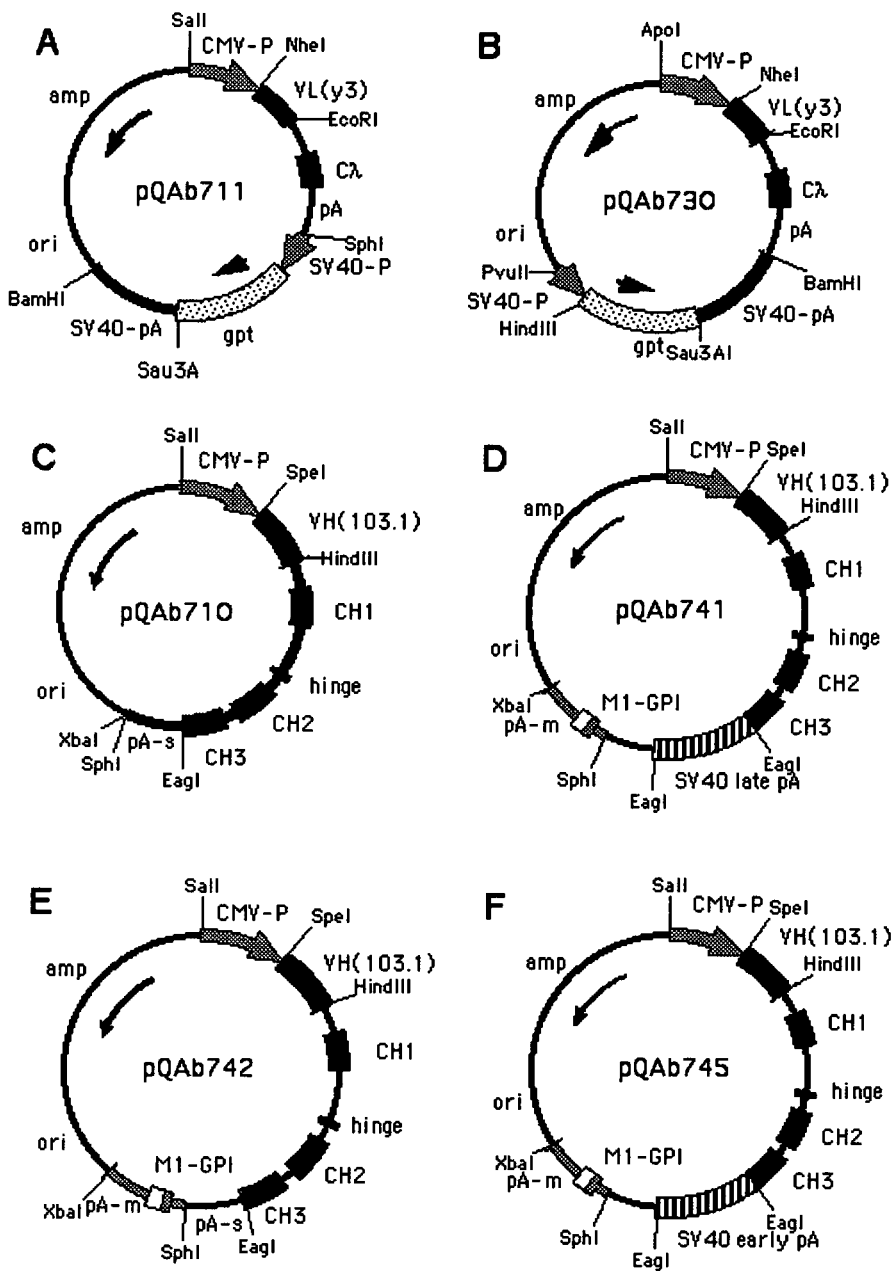
FIG. 2. Expression vectors coding for immunoglobulin light chains (FIGS. 2A and 2B) and immunoglobulin heavy chains (FIGS. 2C, 2D, 2E and 2F).
Figure 7:
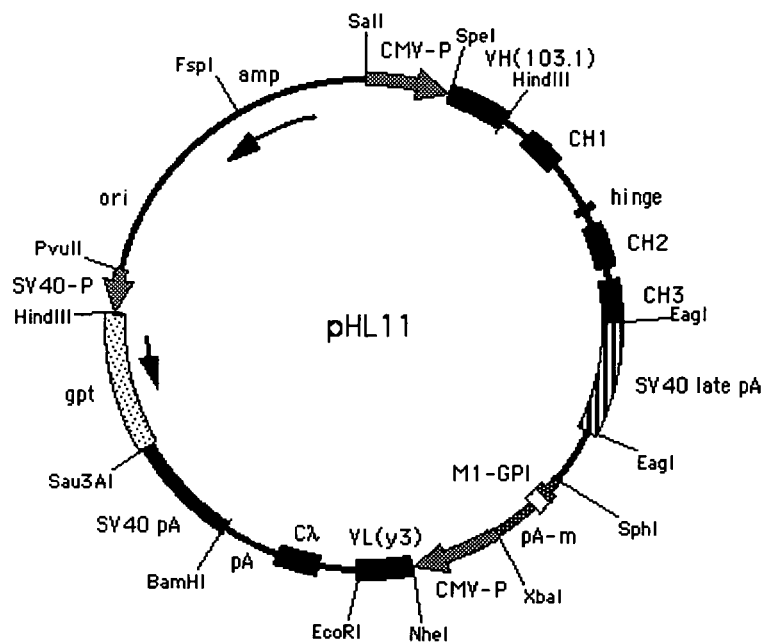
FIG. 7. Expression vector pHL11 used for simultaneous expression of M-form and S-form IgG molecules in NS0 myeloma cells.

For simultaneous expression of membrane-bound and secreted IgG molecules in myeloma cells, the heavy chain gene in pQAb741 (SalI to XbaI; FIG. 2D) was inserted into the SalI site of pQAb730 (FIG. 2B) to construct pHL11 (FIG. 7). For stable expression of IgG molecules, pHL11 was introduced into the chromosome of a mouse myeloma cell line NS0 (European Collection of Animal Cell Cultures, Salisbury, Wiltshire, UK). NS0 cells were grown in DME medium containing 10% FBS at 37° C. in a 7.5% $CO_2$ incubator. Electroporation of FspI-digested pHL11 into NS0 cells was carried out essentially as described previously (Bebbington et al., *Biotechnology* 10:169-175 (1992)). Transfected cells were appropriately diluted in DME medium containing 10% FBS and plated in 96-well plates. Twenty four hours after transfection, selection media (DME medium containing 10% FBS, HT media supplement (Sigma, St. Louis, Mo.), 0.25 mg/ml xanthine and 1 µg/ml mycophenolic acid) was applied. NS0 stable transfectants that appeared to have been derived from a single transfectant, thus clonal, were expanded in DME medium containing 10% FBS.

Figure 8:
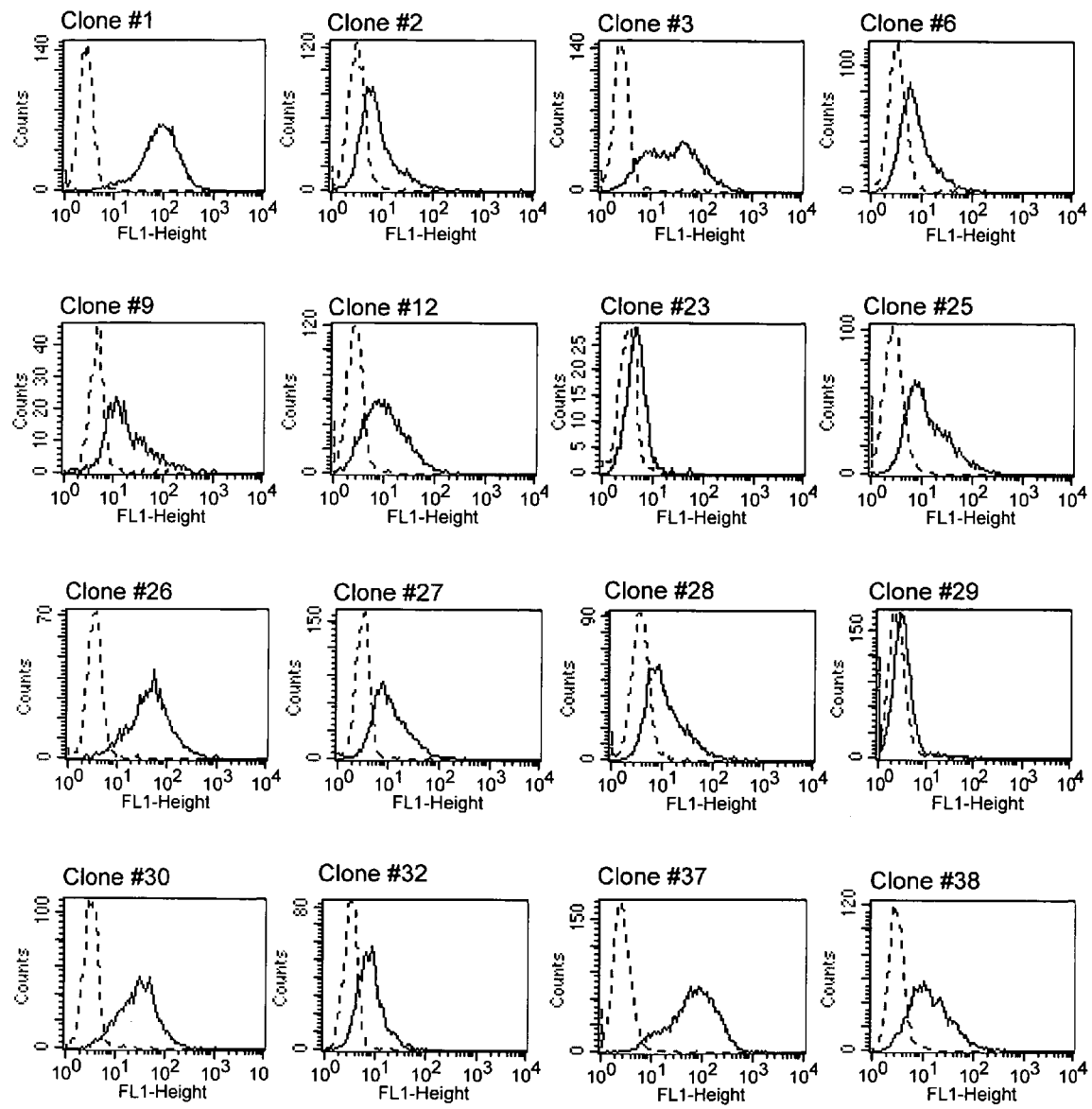
FIG. 8. Flow cytometry analysis of expression levels of IgG molecules on the surface of various NS0 stable transfectant clones.
Figure 10:
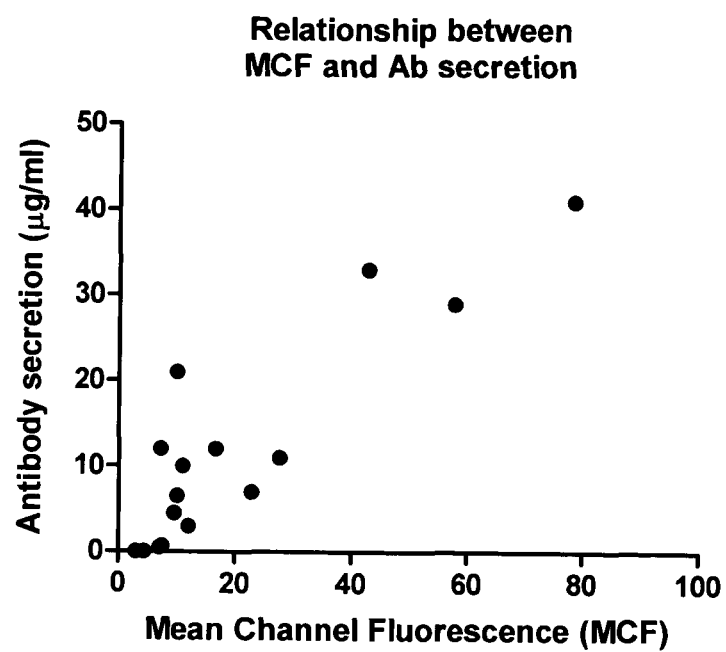
FIG. 10. Correlation plot of corresponding MCF values and antibody secretion levels for each NS0 transfectants in FIG. 9.

Expression of IgG molecules on the surface of each NS0 stable transfectant was analyzed by flow cytometry as described supra. The result is shown in FIG. 8. In each panel, unstained cells are represented by broken line, and cells stained with FITC-labeled goat anti-human IgG antibody are represented by solid line. Each NS0 transfectant showed a different level of shift when stained with FITC-labeled goat anti-human IgG antibody. Geometrical mean channel fluorescence (MCF) of each NS0 transfectant stained with FITC-labeled goat anti-human IgG antibody is shown in FIG. 9. Expression of IgG molecules in culture supernatant of each NS0 transfectant was measured by ELISA as described hereinabove. The ELISA result is summarized in FIG. 9. When the MCF value was plotted against the antibody secretion level for each NS0 transfectant, a strong correlation was observed between the expression levels of membrane-bound and secreted IgG molecules (correlation coefficient r=0.89, P<0.0001) (FIG. 10), indicating that the IgG secretion level of each stable transfectant is predictable from the MCF value.

Figure 11:
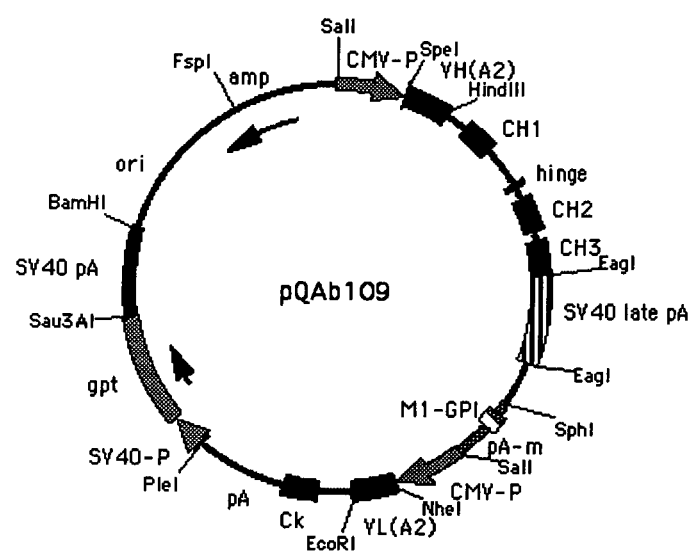
FIG. 11. Expression vector pQAb 109 used for expression of mouse-human chimeric anti-TNFalpha monoclonal IgG1/kappa antibody.

Simultaneous Expression of the Membrane-Bound and Secreted Forms of Anti-TNFalpha Monoclonal Antibodies VH and VL genes of the mouse anti-TNFalpha monoclonal antibody A2 (Knight, D. M., et al., *Mol Immunol* 30, 1443-1453 (1993)) were synthesized as exons, each carrying an appropriate signal peptide, a splice donor signal at the 3' end, and appropriate flanking restriction enzyme sites (NheI and EcoRI for VH, SpeI and HindIII for VL). The synthesized VH and VL genes were digested with corresponding restriction enzymes and cloned into a mammalian expression vector to generate pQAb109 for expression of mouse-human chimeric anti-TNFalpha monoclonal IgG/kappa antibody (FIG. 11A). The expression vector pQAb109 was constructed to carry the following genetic components. Proceeding clockwise from the SalI site at the top, pQAb 109 carries the heavy chain transcription unit (from SalI to SalI) derived from the SalI-XbaI fragment of pQAb741 that allows simultaneous expression of the membrane-bound and secreted forms of heavy chains, except that the VH(103.1) exon was replaced with the A2 VH exon (VH(A2)) in pQAb109. Following the heavy chain transcription unit is the light chain transcription unit (SalI to PleI), which is composed of the CMV promoter (SalI to NheI), the A2 VL exon (VL(A2); NheI to EcoRI), and a genomic sequence containing the human kappa light chain constant region exon (Ck) with part of the intron preceding it and a poly(A) site after Ck (EcoRI to PleI). Moving clockwise further, pQAb 109 carries the gpt transcription unit (PleI to BamHI) and the pUC18-derived fragment carrying the replication origin in *E. coli* and the beta lactamase gene (BamHI to SalI), both of which derived as a unit from the SphI-SalI fragment of pQAb711 (FIG. 2A).

For stable expression of chimeric anti-TNFalpha antibodies, NS0 cells were transfected with FspI-digested pQAb109 by electroporation and stable transfectants were selected in the presence of mycophenolic acid as described in the previous section. Expression of chimeric anti-TNFalpha antibodies on the surface of each NS0 stable transfectant was analyzed by flow cytometry as described above. Each NS0 transfectant showed a different level of shift when stained with FITC-labeled goat anti-human IgG antibody when compared to unstained cells. Geometrical mean channel fluorescence (MCF) of each NS0 transfectant stained with FITC-labeled goat anti-human IgG antibody is shown in FIG. 12.

Expression of chimeric anti-TNFalpha antibodies in the growth medium of each NS0 transfectant was measured by sandwich ELISA using goat anti-human IgG Fc gamma chain-specific polyclonal antibody (SouthernBiotech) for coating and goat anti-human kappa chain polyclonal antibody (SouthernBiotech) for detection of bound chimeric anti-TNFalpha IgG1/kappa antibody. Human IgG1/kappa myeloma protein (SouthernBiotech) was used as a standard. The result is summarized in FIG. 12. Both membrane-bound and secreted forms of chimeric anti-TNFalpha antibodies were simultaneously expressed in the majority of NS0 stable transfectants. When the MCF value was plotted against the antibody secretion level for each NS0 transfectant, a good correlation was observed between the expression levels of membrane-bound and secreted chimeric anti-TNFalpha antibodies (correlation coefficient r=0.68, P=0.0006).

Figure 13:
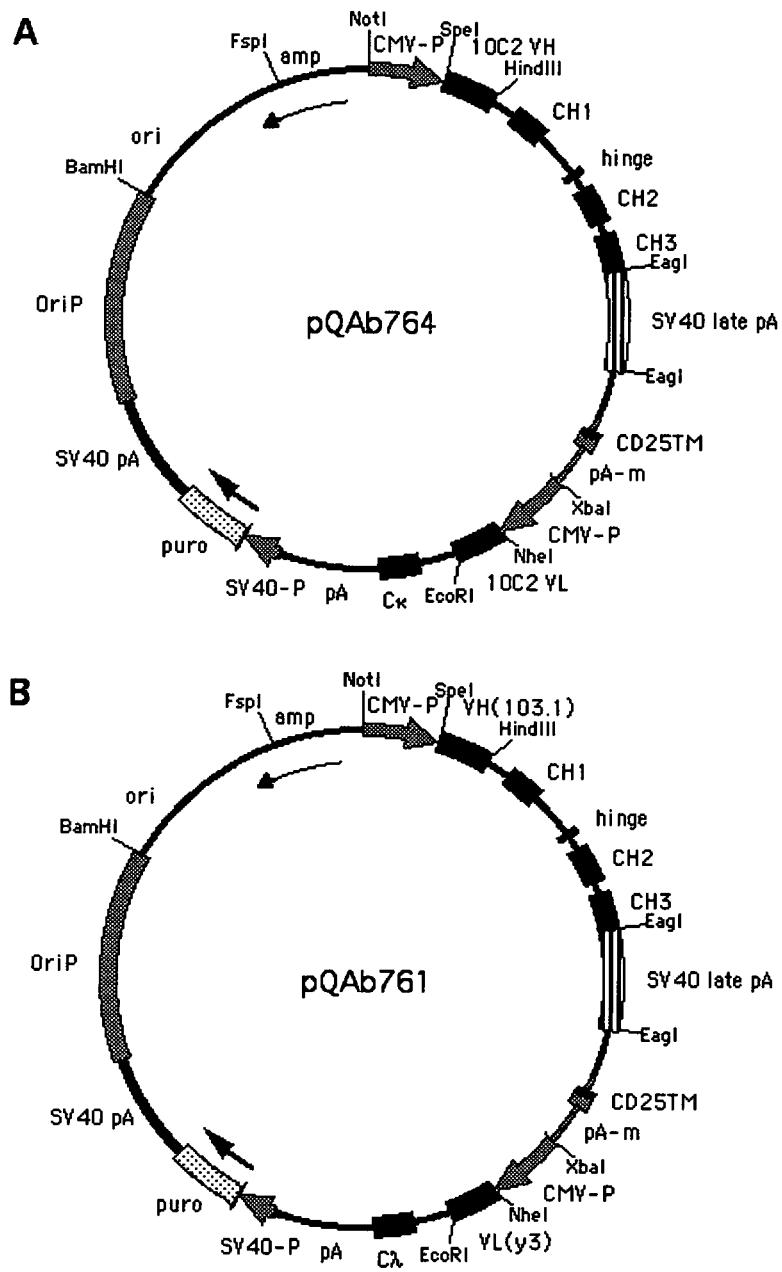
FIG. 13. Expression vector pQAb764 (FIG. 13A) used for expression of chimeric anti-CD122 IgG1/kappa monoclonal antibody and pQAb761 (FIG. 13B) for expression of chimeric IgG1/lambda monoclonal antibody.

Simultaneous Expression of Membrane-Bound and Secreted Forms of Anti-CD122 Monoclonal Antibodies VH and VL cDNAs of a mouse anti-human CD122 monoclonal antibody 10C2, which was isolated at JN Biosciences LLC (Mountain View, Calif.) using a standard hybridoma technology, were modified to the form of exons, each carrying an appropriate signal peptide, a splice donor signal at the 3' end, and appropriate flanking restriction enzyme sites (NheI and EcoRI for VH, SpeI and HindIII for VL). The resulting 10C2 VH and VL genes were digested with appropriate restriction enzymes and cloned between corresponding sites of a derivative of pQAb109 for expression of mouse-human chimeric anti-CD122 IgG/kappa monoclonal antibody. The resultant plasmid was named pQAb764 (FIG. 13A). Compared to pQAb109, pQAb764 carries (i) the human CD25 transmembrane and cytoplasmic domains in place of the GPI membrane anchorage signal, (ii) the puro gene encoding puromycin N-acetyl-transferase in place of the gpt gene, and (iii) the replication origin of Epstein-Barr virus (OriP) (Margolskee et al., *Mol Cell Biol* 8: 2837-2847 (1988)).

For control, another expression vector, pQAb761 (FIG. 13B), was constructed. The structure of pQAb761 is identical to that of pQAb764, except that the heavy and light chain genes in pQAb761 derived from pQAb109. Antibodies produced from pQAb761 do not bind to human CD122.

Human 293c18 cells (CRL-10852; ATCC, Manassas, Va.) were transfected with pQAb764 using Lipofectamine 2000 (Invitrogen) following manufacturer's protocol. Stable transfectants selected in DME medium containing 10% FBS and 1 µg/ml puromycin were grown in bulk (293c18/pQAb764). Following the same procedure, 293c18 cells stably transfected with pQAb761 (293c18/pQAb761) were generated.

Figure 14:
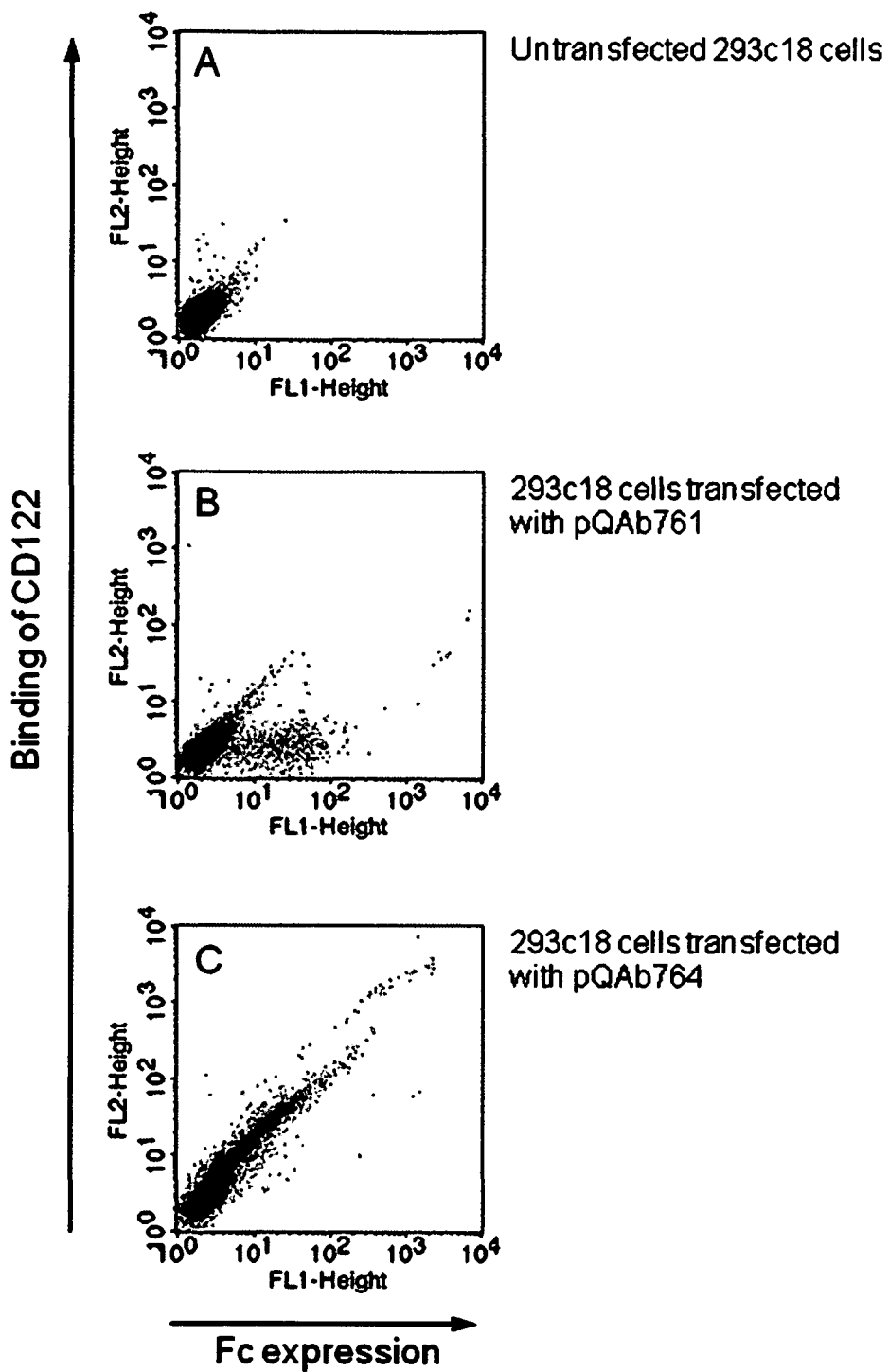
FIG. 14. Flow cytometry analysis of untransfected 293c18 cells (FIG. 14A), a mixture of 293c18 cells stably transfected with pQAb761 (FIG. 14B), and a mixture 293c18 cells stably transfected with pQAb764 (FIG. 14C) for presence of membrane-bound antibodies.

293c18/pQAb764 and 293c18/pQAb761 cells were analyzed by FACS to examine the expression of chimeric 10C2 antibody on the cell surface. Cells were stained simultaneously with (i) FITC-labeled goat anti-human IgG gamma chain polyclonal antibody and (ii) human CD122-mouse Fc (CD122-mFc) fusion proteins followed by phycoerythrin (PE)-labeled goat anti-mouse IgG gamma chain polyclonal antibody. CD122-mFc fusion proteins are composed of the extracellular region of human CD122 and the Fc region of mouse gamma-1 heavy chain. As shown in FIG. 14C, expression of chimeric 10C2 antibody on the surface of 293c18/pQAb764 cells was confirmed in two fashions: (i) binding of goat anti-human IgG gamma chain antibody (X axis), which represents the expression of the Fc region, and (ii) binding of CD122-mFc fusion proteins (Y axis), which represents the expression of the antigen binding site. 293c18/pQAb761 cells bound to FITC-labeled goat anti-human IgG gamma chain polyclonal antibody, but not to CD122-mFc fusion proteins (FIG. 14B). Binding of neither goat anti-human IgG gamma chain antibody (X axis) nor CD122-mFc fusion protein (Y-axis) was detected with untransfected 293c18 cells (FIG. 14A).

Culture supernatants of 293c28/QAb764 cells were subjected to ELISA to analyze the expression of secreted antibodies. ELISA was carried out as described above using goat anti-human IgG gamma chain antibody for coating and HRP-conjugated goat anti-human kappa chain antibody for detection. The expression level of chimeric 10C2 monoclonal antibodies in the culture supernatant was 4.9 µg/ml. Such produced chimeric 10C2 antibodies showed specific binding to human CD122. Thus, 293c18/pQAb764 cells simultaneously produced membrane-bound and secreted forms of functional anti-CD122 monoclonal antibodies.

Enrichment of Cells Expressing Anti-CD122 Monoclonal Antibodies on the Surface

Figure 15:
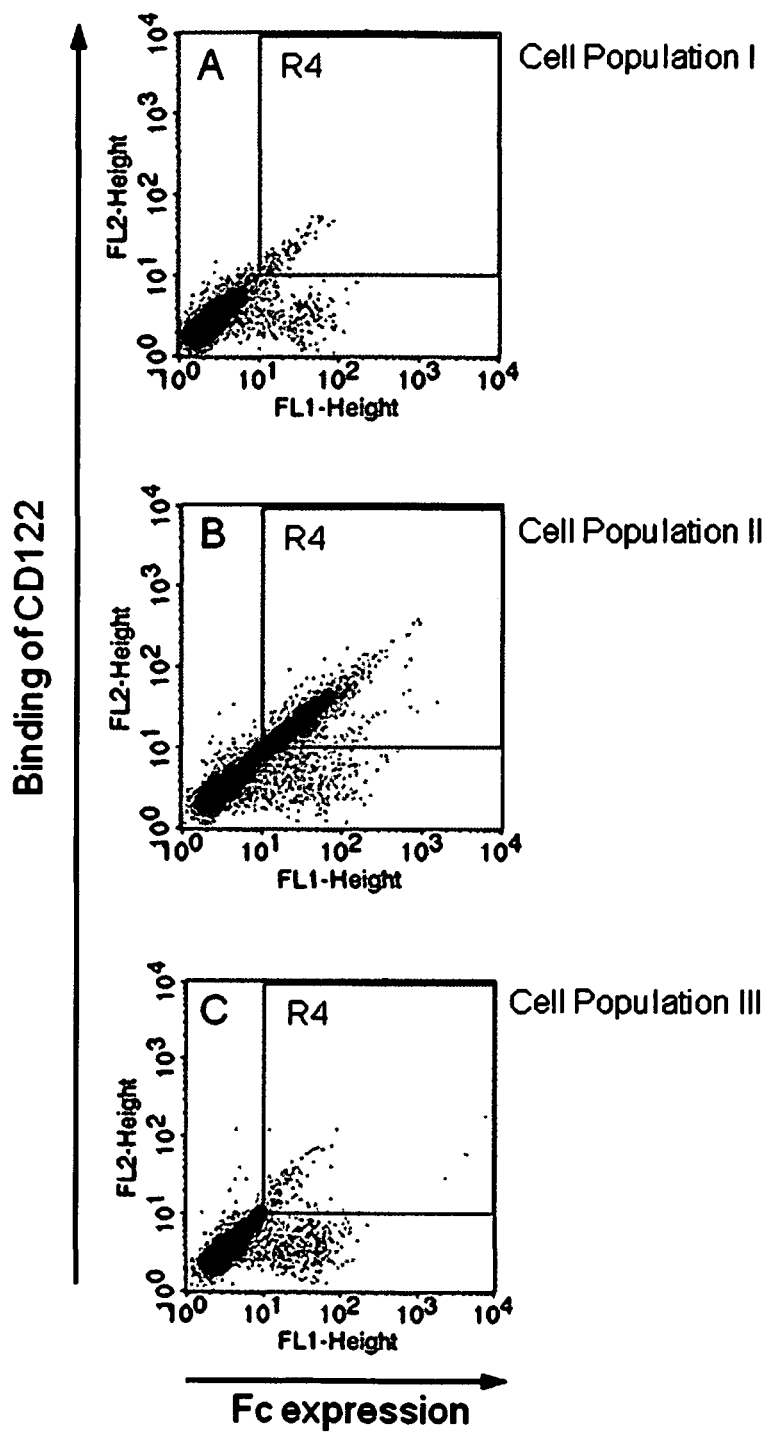
FIG. 15. Flow cytometry analysis of a mixture of 293c18 cells stably transfected with each of pQAb761 and pQAb764 for presence of membrane-bound anti-CD122 antibodies without (FIGS. 15A and 15C) or with (FIG. 15B) enrichment using magnetic beads coated by recombinant soluble human CD122.

293c18/pQAb761 and 293/pQAb764 cells were mixed with a 99:1 ratio. Such mixed cells (Cell Population I) were stained simultaneously with (i) FITC-labeled goat anti-human IgG gamma chain polyclonal antibody and (ii) human CD122-mouse Fc (CD122-mFc) fusion proteins followed by PE-labeled goat anti-mouse IgG gamma chain polyclonal antibody. As shown in FIG. 15A, 0.6% of cells were observed as expressing anti-CD122 antibodies on the surface (R4 region).

Approximately two million cells of Cell Population I were subjected to binding to anti-mouse IgG-conjugated DYNAL magnetic beads (Invitrogen) precoated with CD122-mFc fusion proteins in PBS containing 0.5% BSA (Buffer I). After washing with Buffer I, cells captured by magnet were recovered and grown in DME medium containing 10% FCS and 1 µg/ml puromycin for 12 days (Cell Population II). In parallel, Cell Population I was grown in DME medium containing 10% FCS 1 µg/ml puromycin for 12 days (Cell Population III). Cell Populations II and III were subjected to FACS analysis as described above to monitor the expression of chimeric anti-CD122 antibodies on the surface. It was found that 24.9% and 0.8% of cells in Cell Populations II and III, respectively, expressed chimeric anti-CD122 antibodies on the surface (FIGS. 15B and 15C).

Cell Populations II and III were further single-cell subcloned by limiting dilution in 96-well plates and grown in DME medium containing 10% FCS and 1 µg/ml puromycin. Chimeric anti-CD122 antibodies were produced in culture supernatant by 13 out of 30 subclones (43.3%) of Cell Population II and 3 out of 90 subclones (3.3%) of Cell Population III. Thus, cells expressing anti-CD122 antibodies on the surface were efficiently enriched by one round of selection with magnet beads coated by CD122-mFc fusion proteins.

Isolation of Antibodies with Desired Binding Properties

A mammal, such as mouse, rat, hamster, goat, sheep and rabbit, or a bird, such as chicken, quail, duck and pigeon, is immunized with an antigen of interest using standard procedures. RNA is extracted from B cells of such immunized mammal or bird, and cDNA is synthesized using standard procedures. Regions encoding VH (or VL) are amplified by PCR using such generated cDNA as a template, a 5' primer that binds to the N-terminal region of VH (or VL) and has an appropriate restriction enzyme site at the end, and a 3' primer that binds to the C-terminal region of VH (or VL), carries a splicing donor site and has an appropriate restriction enzyme site at the end. Alternatively, VH and VL exons are synthesized using published procedures. For construction of antibody libraries, PCR-amplified VH-coding regions (or synthetic VH exons) are cloned between the SpeI and HindIII sites and PCR-amplified VL-coding regions (or synthetic VL exons) are cloned between the NheI and EcoRI sites in pHL11 (FIG. 7) or pQAb761 (FIG. 13B) for production of antibodies in the IgG1/lambda form, in pQAb109 (FIG. 11) or pQAb764 (FIG. 13A) for production in the IgG1/kappa form, or in a derivative of pHL11, pQAb 109, pQAb761 or pQAb764 carrying a heavy chain gene other than human gamma-1, a light chain gene other than human kappa and lambda, and/or a selectable marker other than the gpt and puro genes.

Figure 16:
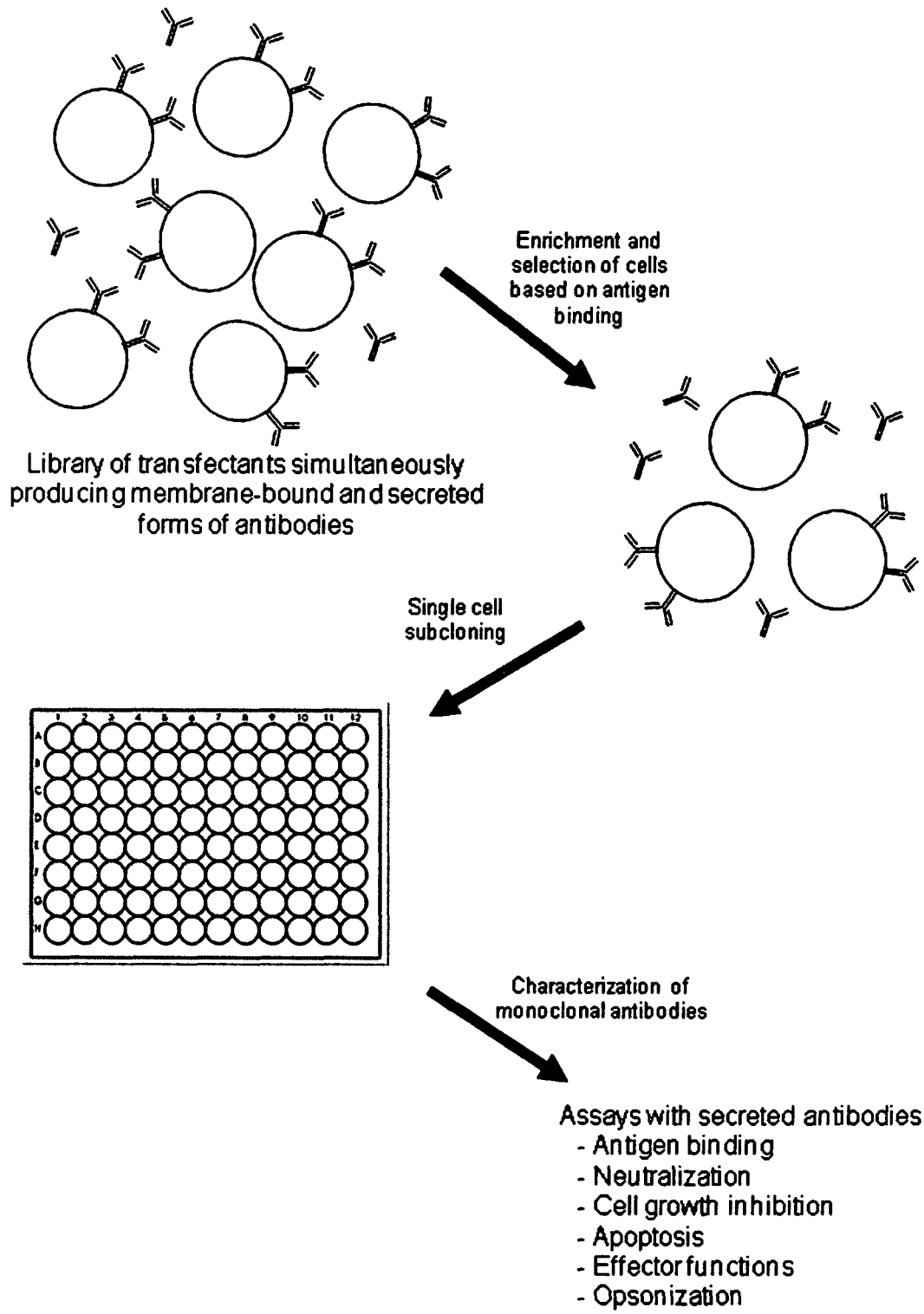
FIG. 16. Schematic of streamlined selection scheme provided by the present invention showing enrichment of transfectants expressing desirable M-form antibodies, followed by single cell subcloning, and characterization of biological function(s) of S-form antibodies.

Such generated library plasmid DNA is transfected into eukaryotic cells, e.g., NS0 and HEK293 cells, using standard procedures. Such transfected cells are mixed together and grown under a selective condition, e.g., in mycophenolic acid media, to select stable transfectants. As illustrated in FIG. 16, cells producing antibodies on the surface are subjected to selection and enrichment based on the ability to bind specifically to a desired antigen, for example, using a cell sorter or magnetic beads. Stable transfectants showing specific binding to the antigen are subcloned in 96-well plates by a standard procedure, for example, using a cell sorter or limiting dilution. Antibodies secreted in culture supernatant of each subclone are tested for specificity and affinity of antigen binding, effector functions such as ADCC and CDC, and biological activities such as blocking of ligand-receptor interaction, inhibition of cell growth, stimulation of cell growth, apoptosis induction, and viral neutralization. Stable transfectants expressing monoclonal antibody with desired properties are expanded. Monoclonal antibodies are purified from culture supernatant of each subclone using standard procedures for further characterization.

Modulation of the Antigen-Binding Affinity of a Monoclonal Antibody

VH and VL genes of a monoclonal antibody to be modified in its binding characteristics are first cloned into a vector, such as pHL11 and pQAb109, for simultaneous expression of the membrane-bound and secreted forms of the antibody. The VH and/or VL genes are then mutagenized using standard procedures and cloned back into the expression vector to make a library of variant antibodies. The library DNA is transfected into cells and stable transfectants are isolated. Alternatively, pHL11- or pQAb109-derived vector that expresses a monoclonal antibody of interest is introduced into a cell that is capable of altering the variable region sequences, for example, a stable transfectant carrying the activation-induced cytidine deaminase (AID) gene (Martin et al., *Proc Natl Acad Sci* 99: 12304-12308, (2002)).

For isolation of variant antibodies with altered binding affinities, stable transfectants are subjected to binding to antigen (for monitoring the level of antigen binding of the variant antibody expressed on the cell surface) and anti-Ig antibodies (for monitoring the level of antibody expression on the cell surface) as described previously (Akamatsu, Y., et al., supra (2007)). By comparing the ratio between antigen binding and Ig expression on the surface, cells expressing antibodies with higher (or lower) binding affinities are selected and subcloned, for example, using a cell sorter. Such selected cells are expanded and antibodies are purified from culture supernatant of each subclone using standard procedures for further characterization of antigen binding affinities.

For isolation of variant antibodies with altered binding specificities, stable transfectants expressing variant antibodies on the surface are subjected to binding to an antigen to which the parental antibody does not bind (or only weakly binds). Stable transfectants showing specific binding to the antigen are subcloned. Antibodies secreted in culture supernatant of each subclone are tested for specificity and affinity of antigen binding. Stable transfectants expressing antibodies with desired properties are expanded. Antibodies are purified from culture supernatant using standard procedures for further characterization.

Use of Different Membrane-Binding Signals

The GPI anchorage signal derived from the human CD55 gene in the synthetic M1-GPI exon carried by HL11 and pQAb109 was replaced with the membrane localization signal of the transmembrane region of the human CD25 in pQAb764. Chimeric anti-CD122 monoclonal antibody encoded in pQAb764 was simultaneously expressed on the cell surface (FIG. 14) and in culture supernatant as described above.

Moreover, the GPI anchorage signal in pHL11 and pQAb108 as well as the CD25-derived membrane localization signal in pQAb764 is replaced with another membrane localization signal of the transmembrane region of the CD4, CD8 CD16, CD62P, CD122 TNF receptor type I, CD20, CCR5 and CXCR4 genes of any mammalian species. Such modified gene is transfected into cells, with an immunoglobulin light chain gene, and the expression of membrane-bound and secreted forms of antibodies is analyzed with standard procedures.

Expression of Fc Fusion Proteins

Figure 17:
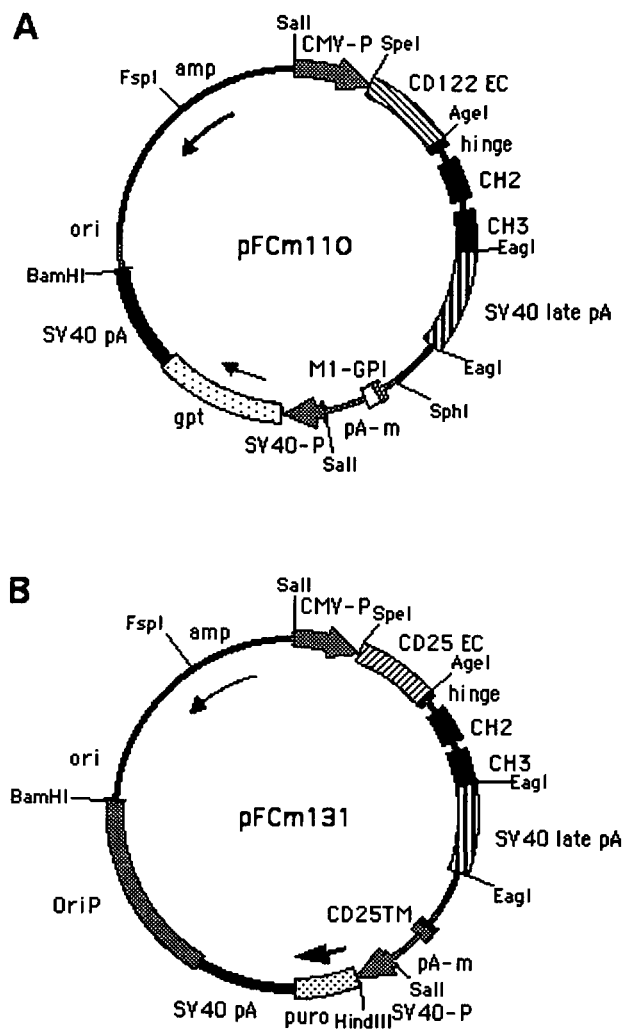
FIG. 17. Expression vectors pFCm110 (FIG. 17A) for simultaneous expression of M-form and S-form of human CD122-Fc fusion proteins and pFCm131 (FIG. 17B) for simultaneous expression of M-form and S-form of human CD25-Fc fusion proteins.

The artificial gene of this invention is applicable to simultaneous expression of any proteins in both membrane-bound and secreted forms. As an example, pFCm110 (FIG. 17A), a derivative of pQAb109 (FIG. 11), was constructed for expression of CD122-Fc fusion proteins. The region carrying the VH, CH1 and CH2 exons, including the CH2-hinge intron, was removed from pQAb109, and cDNA encoding the extracellular region of human CD122 (CD122 EC) was inserted in such a way to fuse its C-terminus in frame to the hinge region. In addition, the light chain transcription unit (XbaI to BamHI) was removed to generate pFCm110. NS0 cells were transfected with pFCm110 by electroporation. Stable transfectants were selected in DME medium containing 10% FBS, HT media supplement, 0.25 mg/ml xanthine and 1 µg/ml mycophenolic acid as described above. Expression of CD122-Fc fusion proteins in culture supernatant of each NS0 stable transfectant was measured by ELISA using goat anti-human IgG gamma chain antibody for coating and HRP-conjugated goat anti-human IgG gamma chain antibody for detection of bound CD122-Fc fusion proteins. As a standard, purified TNFRI-Fc fusion proteins, in which the extracellular region of human TNF receptor type I is fused to the Fc region of human gamma-1 chain, was used. Expression of CD122-Fc fusion proteins on the cell surface was analyzed by flow cytometry using biotinylated goat anti-human IgG Fc chain antibody (Jackson ImmunoResearch West Grove, Pa.) and PE-labeled streptavidin (SouthernBiotech). FIG. 18 summarizes surface expression and secretion of CD122-Fc fusion protein in each stable transfectant. NS0 stable transfectants that secreted CD122-Fc fusion protein in culture supernatants always expressed CD122-Fc on the surface.

Figure 19:
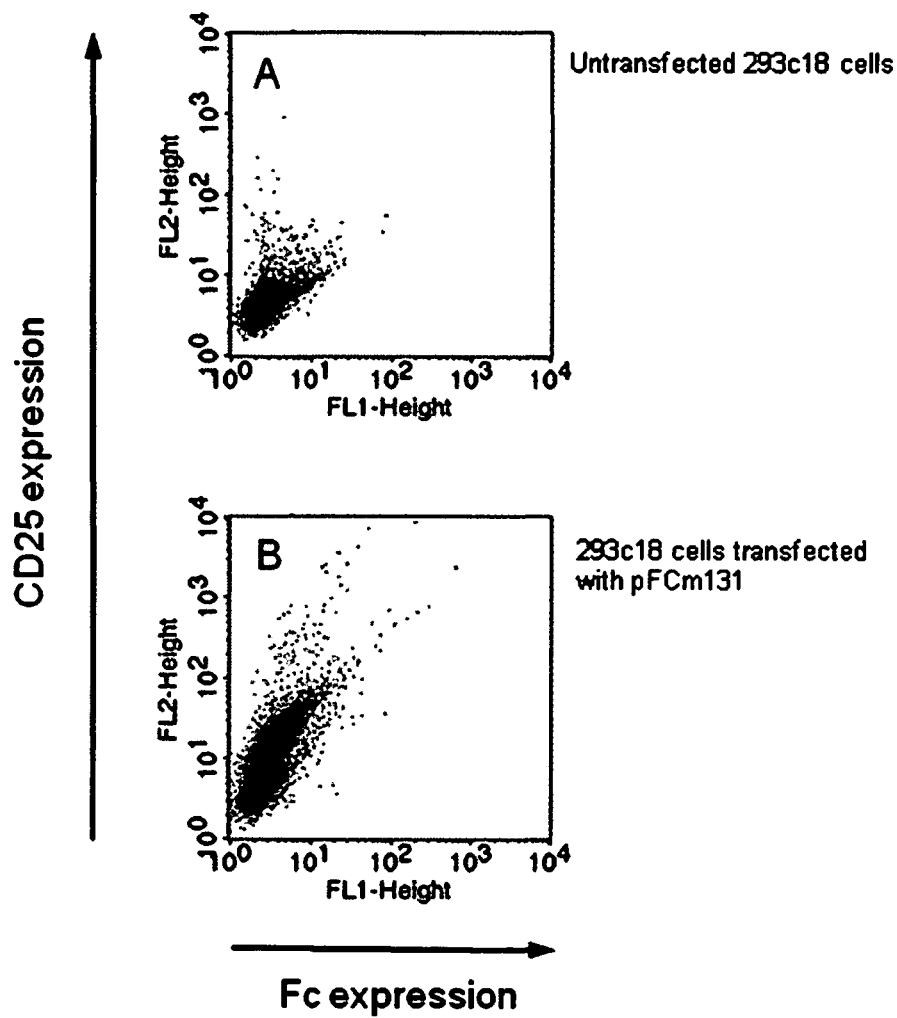
FIG. 19. Flow cytometry analysis of untransfected 293c18 cells (FIG. 19A) and a mixture of 293c18 stable transfectants of the expression vector pFCm131 shown in FIG. 17B (FIG. 19B) for presence of cell surface expression of the anti-CD122 antibody.

For expression of CD25-Fc fusion proteins simultaneous in the secreted and membrane-bound forms, pFCm110 was modified in such a way that (i) the SpeI-AgeI fragment was replaced with cDNA encoding the extracellular region of human CD25, (ii) the region encoding the GPI anchorage signal was replaced with cDNA encoding the human CD25 transmembrane and cytoplasmic regions, (iii) the gpt gene was replaced with the puro gene, and (iv) the replication origin of Epstein-Barr virus (OriP) was inserted into the BamHI site. The resultant expression vector, pFCm131 (FIG. 17B), was transfected into 293c18 cells using Lipofectamine 2000 (Invitrogen). Culture supernatant of a mixture of puromycin-resistant 293c18 cells was analyzed by ELISA to measure the production level of soluble CD25-Fc fusion proteins as described above using purified CD122-Fc fusion protein as standard. The level of CD25-Fc fusion proteins in culture supernatant was 0.3 μg/ml. To monitor the expression of CD25-Fc fusion proteins on the surface, puromycin-resistant 293c18 cells were stained with FITC-labeled goat anti-human IgG gamma chain antibody (Southern Biotech) and PE-labeled mouse anti-human CD25 monoclonal antibody (R&D Systems, Minneapolis, Minn.) and then analyzed by flow cytometry. As shown in FIG. 19B, 293c18 cells stable transfected with pFCm131 also expressed CD25-Fc fusion proteins on the surface.

The SpeI-Age fragment in pFCm110 was replaced with cDNA encoding the extracellular region of human CD132 (CD132 EC) to construct pFCm115 for expression of CD132 EC fused to the Fc region of human gamma-1 chain (CD132-Fc). NS0 cells were stably transfected with pFCm115 as described above. Two of such generated NS0 stable transfectants, clones 1F2 and 3C7, were analyzed for expression of CD132-Fc fusion protein in culture supernatant and on the surface by ELISA and FACS, respectively, as described above. The production level of CD132-Fc fusion proteins in culture supernatants was 2.3 and 0.2 μg/ml for clones 1F2 and 3C7, respectively, in ELISA using purified CD122-Fc as standard. When cells were stained with biotinylated goat anti-human IgG gamma chain antibody followed by PE-labeled streptavidin, MCF values of clones 1F2 and 3C7 was 18.5 and 16.2, respectively. The MCF value of untransfected NS0 cells stained in the same manner was 5.3. Thus, NS0 stably transfected with pFCm115 simultaneously expressed secreted and membrane-bound forms of CD132-Fc fusion proteins.

For expression of other Fc fusion proteins simultaneously in both secreted and membrane-bound forms, the SpeI-AgeI fragment encoding the extracellular region of human CD122 in pFCm110 or that of human CD25 in pFCm131 is replaced with the DNA fragment encoding the entire or a part of the extracellular region of cell surface receptor molecules, such as human TNF receptor type I and type II, LFA3 and CTLA-4. Alternatively, cytokine-Fc fusion proteins, including interleukin 2 (IL2)-Fc fusion and IL15-Fc fusion, are expressed using pFCm110- and pFCm131-derived vectors. These vectors are introduced into eukaryotic cells for simultaneous expression of membrane-bound and secreted forms of Fc fusion proteins.

Figure 20:
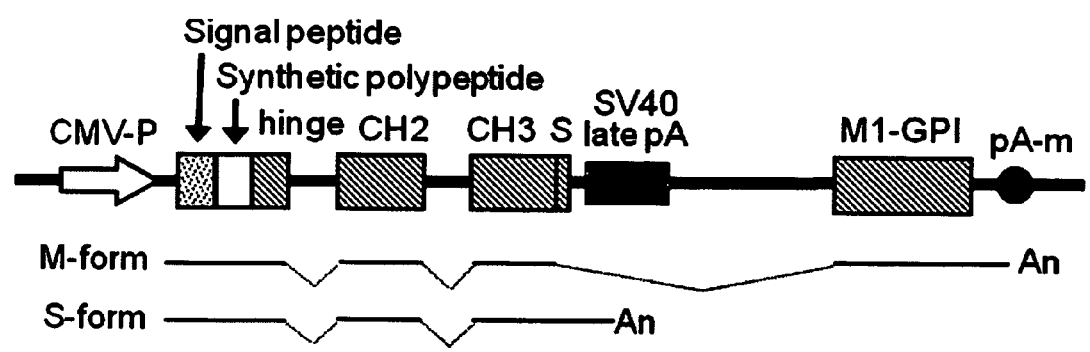
FIG. 20. Schematic representation of an expressible sequence coding for both an M-form and an S-form of a synthetic polypeptide-Fc fusion protein.

Simultaneous Expression of Membrane-Bound and Secreted Forms of Polypeptide-Fc Fusion Proteins DNA fragments encoding a polypeptide with the length of more than two amino acids are synthesized. Such coding regions are fused at the N-terminus to a signal peptide-coding region and at the C-terminus to the hinge region in pFCm110 (or its derivative) and placed downstream the CMV promoter (FIG. 20). For making a library of variant polypeptides, the coding region of the polypeptide is mutagenized using standard procedures. The generated plasmids, which represent a collection of variants of the original polypeptide, are transfected into eukaryotic cells, e.g., HEK293 and NS0 cells, in such a way that each transfectant expresses both the membrane bound and secreted form of a single variant of the original polypeptide. Cells expressing variant polypeptide-Fc fusion proteins with desired binding properties are selected using a cell sorter, magnet beads and other appropriate methods. Polypeptide-Fc fusion proteins secreted from the subclones are used for further characterization of their binding and biological properties.

Figure 21:
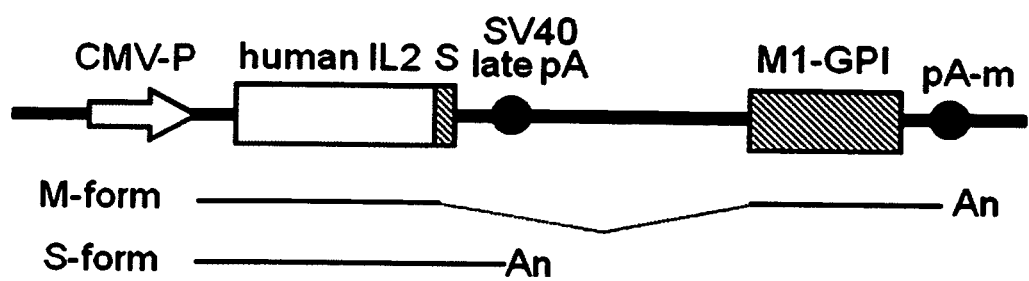
FIG. 21. Schematic representation of an expressible sequence coding for both an M-form and an S-form of human IL-2 protein.

Simultaneous Expression of Polypeptides in the Membrane-Bound and Secreted Forms Any polypeptide can be simultaneously expressed in the membrane-bound and secreted forms as non-Fc fusion proteins using pFCm110-derived vectors. As an example, the coding region of human IL2 is fused in frame to the S coding region in pFCm110 with or without a flexible polypeptide linker between the two regions (FIG. 21) in such a way that a splicing donor signal is generated at the junction between the IL2-coding and S regions in such a way that splicing connects the IL2- and M1-GPT coding regions. Such generated plasmid is transfected to eukaryotic cells such as HEK293 and NS0, and expression of secreted and membrane-bound forms of IL2 is monitored using standard procedures. The IL2-coding region is then mutagenized using standard procedures and introduced into eukaryotic cells for stable expression of variant IL2 molecules. Cells expressing variant IL2 with desired binding properties on the surface are selected using a cell sorter, magnetic beads and other appropriate methods. Variant IL2 molecules purified from culture supernatants of selected cells are used for further characterization of their binding and biological properties.

Using such pFCm110-derived vectors, other non-Fc fusion proteins, such as cytokines, chemokines, growth factors, receptors, and cytoplasmic proteins, including human IL1, human IL15 and human growth hormone, can be expressed simultaneously in membrane-bound and secreted forms in eukaryotic cells.

Transgenic Animals Simultaneously Expressing Both Membrane-Bound and Secreted Antibodies in Plasma Cells.

An Ig mu gene 3' region mimetic is used to replace the 3' region of a mouse immunoglobulin heavy chain gene, such as gamma-1, gamma-2a, gamma-2b, gamma-3, alpha and epsilon genes, in the chromosome of mouse embryonic stem cells using experimental procedures commonly employed in the art. Transgenic mice that produce both membrane-bound and secreted forms of antibodies in plasma cells are then generated using such constructed mouse embryonic stem cells. Such generated transgenic mice are immunized with an antigen of interest. B cells of such immunized mice, which produce both membrane-bound and secreted forms of monoclonal antibodies, are immortalized, for example, by fusing with myeloma cells or introducing an oncogene. Such immortalized cells are selected based on binding to the antigen and subcloned. Monoclonal antibodies secreted in the culture supernatant of each subclone are further characterized for binding characteristics and biological functions.

Cell Lines Capable of VDJ Recombination that Express Both Membrane-Bound and Secreted Antibodies An Ig mu gene 3' region mimetic of this invention is used to replace the 3' region of a germ line immunoglobulin heavy chain gene, such as mu, gamma, alpha and epsilon genes, of an animal. Such generated heavy chain gene, also carrying germ line V, D and J segments, together with a germ line kappa or lambda light chain gene of the same or another animal, is introduced into a cell, for example, a HEK293 cell carrying RAG1 and RAG2 transgenes (Oettinger et al, *Science* 248: 1517-1523 (1990)), which is active in VDJ recombination. Cells producing antibodies on the surface are subjected to selection and enrichment based on the ability to bind specifically to a desired antigen, for example, using a cell sorter or magnetic beads. Cells showing specific binding to the antigen are subcloned in 96-well plates by a standard procedure. Antibodies secreted in culture supernatant of each subclone are tested for specificity and affinity of antigen binding, effector functions, and biological activities.

We claim:

1. An artificial gene sequence capable of expressing a polypeptide in both membrane-bound form and secreted form in a eukaryotic host cell, wherein said artificial gene sequence comprises from 5' to 3' direction, the coding region for said polypeptide and an Ig mu gene 3' region mimetic, wherein said Ig mu gene 3' region mimetic comprises from 5' to 3' direction 1) an exon carrying an Ig gamma splicing donor signal, 2) a termination codon downstream of said splicing donor signal, 3) a first polyadenylation signal comprising the SV40 late polyadenylation signal, 4) an exon carrying an Ig mu splicing acceptor signal and encoding a membrane-anchoring sequence, and 5) a second polyadenylation signal from an Ig mu, wherein said polypeptide is selected from the group consisting of an immunoglobulin gamma heavy chain and an Fc gamma fusion protein.

2. The artificial gene sequence of claim 1, wherein said exon carrying an Ig gamma splicing donor signal comprises a CH3 exon of an Ig gamma gene.

3. An expression vector comprising a nucleotide sequence coding for the immunoglobulin gamma heavy chain of claim 1 and a nucleotide sequence coding for an immunoglobulin light chain, wherein coexpression of both said nucleotide sequence coding for the immunoglobulin gamma heavy chain and said nucleotide sequence coding for the immunoglobulin light chain in a host cell produces a whole antibody that is membrane-bound on the surface of the host cell and a whole antibody that is secreted in the supernatant of the host cell culture.

4. A eukaryotic cell carrying the artificial gene of claim 1 in its chromosome, wherein a polypeptide encoded by said artificial gene is expressed in both membrane-bound form and secreted form.

5. The eukaryotic cell of claim 4, wherein said eukaryotic host cell is a mammalian cell.

6. The eukaryotic cell of claim 4, wherein said eukaryotic cell is capable of altering the gene sequence of said polypeptide to result in a variant of said polypeptide possessing a molecular property different from that of said polypeptide.

7. The eukaryotic cell of claim 4, wherein (i) said polypeptide is an immunoglobulin gamma heavy chain, (ii) said eukaryotic cell expresses an immunoglobulin light chain, which is associated with said immunoglobulin gamma heavy chain to form an immunoglobulin, and (iii) said eukaryotic cell is capable of altering variable region gene sequences of said immunoglobulin gamma heavy and said immunoglobulin light chains to result in a variant of said immunoglobulin possessing a binding property different from that of said immunoglobulin.

8. The eukaryotic cell of claim 4, wherein said polypeptide is an immunoglobulin gamma heavy chain, and wherein said eukaryotic cell is capable of VDJ recombination of immunoglobulin genes.

\* \* \* \* \*